(12) United States Patent
Taniguchi et al.

(10) Patent No.: US 9,512,389 B2
(45) Date of Patent: Dec. 6, 2016

(54) HOP OXIDATION-REACTION PRODUCT, PREPARING METHOD THEREOF AND USE THEREOF

(75) Inventors: Yoshimasa Taniguchi, Yokohama (JP); Yumie Kobayashi, Yokohama (JP); Fumitoshi Manabe, Yokohama (JP); Mikio Katayama, Yokohama (JP)

(73) Assignee: Kirin Holdings Kabushiki Kaisha, Tokyo (JP)

(*) Notice: Subject to any disclaimer, the term of this patent is extended or adjusted under 35 U.S.C. 154(b) by 276 days.

(21) Appl. No.: 13/994,632

(22) PCT Filed: Dec. 15, 2011

(86) PCT No.: PCT/JP2011/079085
§ 371 (c)(1),
(2), (4) Date: Aug. 7, 2013

(87) PCT Pub. No.: WO2012/081676
PCT Pub. Date: Jun. 21, 2012

(65) Prior Publication Data
US 2013/0316068 A1 Nov. 28, 2013

(30) Foreign Application Priority Data
Dec. 15, 2010 (JP) ................. 2010-279933

(51) Int. Cl.
C12C 3/00 (2006.01)
A23L 2/38 (2006.01)
C12C 3/06 (2006.01)
A23L 1/30 (2006.01)
A61K 36/185 (2006.01)

(52) U.S. Cl.
CPC ............. *C12C 3/06* (2013.01); *A23L 1/3002* (2013.01); *A61K 36/185* (2013.01); *A61K 2236/10* (2013.01)

(58) Field of Classification Search
CPC ...... A23L 1/3002; C12C 3/06; A61K 36/185; A61K 2236/10
USPC .................................................. 426/590, 600
See application file for complete search history.

(56) References Cited

U.S. PATENT DOCUMENTS

| | | | |
|---|---|---|---|
| 4,717,580 A * | 1/1988 | Forrest ............... | C12C 3/10 426/520 |
| 2007/0280982 A1* | 12/2007 | Ono et al. ............ | 424/410 |
| 2010/0080862 A1 | 4/2010 | Yajima et al. | |

FOREIGN PATENT DOCUMENTS

| | | |
|---|---|---|
| DE | 1201165 B | 9/1965 |
| JP | 2008-231008 A | 10/2008 |
| JP | 2009-542262 A | 12/2009 |
| WO | WO 03/068205 A1 | 8/2003 |

OTHER PUBLICATIONS

Ashurst et al. J. Inst. of Brew. vol. 72, 1966; 561-569.*
(Continued)

*Primary Examiner* — Michele L Jacobson
*Assistant Examiner* — Subbalakshmi Prakash
(74) *Attorney, Agent, or Firm* — Foley & Lardner LLP

(57) ABSTRACT

The present invention relates to a hop extract having a reduced bitter taste which shows a fat absorption suppressing effect. More specifically the present invention relates to a hop extract oxidation-reaction product obtained by an oxidation-reaction of a hop extract.

9 Claims, 26 Drawing Sheets

(56) References Cited

OTHER PUBLICATIONS

Yajima et al. Prevention of diet-induced obesity by dietary isomerized hop extract containing isohumulones, in rodents. International Journal of Obesity (2005) 29, 991-997.*
Negri, G et al. Brazilian Journal of Pharmacognosy 20(6): 850-859, Dec. 2010.*
International Preliminary Report on Patentability in PCT/JP2011/079085 dated Jun. 27, 2013.
Haseleu, G. et al., "Quantitative Sensomics Profiling of Hop-Derived Bitter Compounds Throughout a Full-Scal Beer Manufacturing Process", J. Agric. Food. Chem., Jun. 7, 2010, 58 (13), p. 7930-9.
Garcia-Villalba, R. et al., Analysis of Hop Acids and Their Oxidized Derivatives and Iso-$\alpha$-acids in Beer by Capillary Eletrophoresis-Eletrospray Ionization Mass Spectrometry. J. Agric. Food Chem., 2006, 54(15), p. 5400-9.
Giuseppina, N. et al., Bitter Acids From Hydroethanolic Extracts of *Humulus lupulus* L., Cannabaceae, Used as Anxiolytic. Brazilian Journal of Pharmacognosy, Dec. 10, 2010, 20(6), p. 850-9.
PCT/JP2011/079085 International Search Report Completed Dec. 28, 2011.
Supplementary European Search Report dated Aug. 13, 2014, in EP 11849749.4.
Office Action issued Aug. 4, 2015, in JP 2012-548836, with English translation.
Office Action issued Feb. 9, 2016, in JP 2012-548836, with English translation.

* cited by examiner

Fig. 11

| Extract used: base material (compounding ratio) Heating temperature, time | IC50 ($\mu$g/ml) | Example | Comparative Example |
|---|---|---|---|
| Iso α acid | 296 | | ○ |
| CO2 extract : TK-16(1:3) 60°C24h | 31.7 | 5 | |
| CO2 extract : FD-101(1:3) 80°C8h | 51.7 | 7 | |
| CO2 extract : #2000(1:3) Room temperature 24h | 69.3 | 8 | |
| CO2 extract : #2000(1:3) 80°C24h | 53.5 | 8 | |
| CO2 extract : #300(1:2) Room temperature 24h | 92.7 | 8 | |
| CO2 extract : #300(1:2) 80°C24h | 74.7 | 8 | |
| CO2 extract : BP55(1:3) 80°C48h | 65.6 | 9 | |
| α acid extract : TK-16(1:3) 80°C24h | 46.6 | 10 | |
| β aroma extract : TK-16(1:3) 80°C24h | 29.0 | 2 | |
| IKE extract : TK-16(1:3) 80°C8h | 72.9 | 12 | |
| IKE extract : TK-16(1:3) 80°C24h | 55.6 | 3 | |
| IKE extract : TK-16(1:3) 80°C48h | 54.5 | 12 | |
| EtOH extract : FD-101(1:3) 80°C24h | 49.4 | 11 | |

HOP OXIDATION-REACTION PRODUCT, PREPARING METHOD THEREOF AND USE THEREOF

CROSS REFERENCE TO RELATED APPLICATIONS

This application is a national phase of PCT/JP2011/079085, filed Dec. 15, 2011, which was published on Jun. 21, 2012, as WO 2012/081676, which claims the benefit of JP Application No. 2010-279933, filed Dec. 15, 2010. The respective contents of these applications are incorporated here by reference in their entirety.

TECHNICAL FIELD

The present invention relates to a hop extract oxidation-reaction product in which bitter and harsh tastes are reduced, a preparing method thereof and use thereof. More specifically, the present invention relates to a food product in which the hop extract oxidation-reaction product is used, and to a lipid absorption suppressing agent having the product as an active ingredient.

BACKGROUND ART

In recent years, many health conscious foods and drinks are developed, and are even commercially available. In order to obtain a genuine product with which a health function can be acknowledged, obviously, a compounded amount needs to be greater than an effective amount. As in the old saying "Bitters do good to the stomach," a so-called functional component which provides a beneficial effect with the human body often has a bitter taste. If that is the case, food and drink containing a functional component in an amount equal to or more than the effective amount will have decreased palatability, resulting in a less attractive product.

A hop, from which bitter taste components in beer originate, is also used as a folk medicine for many years, and various health functions such as a calming effect and a stomachic property are known. When an extract obtained from the hop is included in food and drink in an amount equal to or more than a certain amount, a characteristic intense bitter taste and harsh taste arise, and may spoil palatability.

Many attempts have been reported in order to remove or suppress such a bitter taste. Substances used as a bitter taste-reducing material include phosphatidic acid (Product name "Benecort BMI" Kao Corp.), L-ornithine (Food Science Journal, Vol. 317, p 54, 2004) and the like. However, none of them necessarily shows a strong effect when used alone, and in particular, the bitter taste of the hop extract was difficult to be suppressed. Further, in a masking technology (Japanese Patent Laid-Open No. 2008-99682) in which a sweetening agent such as sucralose and thaumatin is added, a bitter taste was masked by sweetness to some extent, but the use thereof is limited due to its strong sweetness.

In the case of pharmaceutical products, sugar coating is mainly used for a tablet in general. In addition, the film coating technology, microencapsulation and the like are used, but a bitter taste has been difficult to be completely masked. Further, in the case of liquid formulations, such technologies can not be used as in the case of drinks. Therefore, suppression of a bitter taste remains a significant problem in the field of food and drink and pharmaceutical products.

CITATION LIST

Patent Literature

Patent Literature 1: Japanese Patent Laid-Open No. 2008-99682
Patent Literature 2: Japanese Patent No. 4503302

Nonpatent Literature

Nonpatent Literature 1: Food Science Journal, Vol. 317, p 54, 2004
Nonpatent Literature 1: IntJObes (Lond). 2005 August; 29(8): 991-7

SUMMARY OF INVENTION

Problem to be Solved by the Invention

There is a report that iso $\alpha$ acid and the like contained in a hop extract has a PPAR agonist activity, and have a lipid metabolism improving effect via this activity (Japanese Patent No. 4503302). Further, there is a report that iso $\alpha$ acid has a pancreatic lipase inhibitory activity, showing a lipid absorption suppressing effect (IntJObes (Lond). 2005, August; 29(8): 991-7). For these reasons, a hop extract containing hop bitter taste components such as $\alpha$ acid, $\beta$ acid and iso $\alpha$ acid as a main component is a potent health functional material for practical use. However, since iso $\alpha$ acid has an intense bitter taste, and $\alpha$ acid and $\beta$ acid have an intense harsh taste, suppression of the bitter and harsh tastes has been a problem when applied to food and drink and pharmaceutical products.

Means for Solving the Problem

The present inventors find that a hop extract oxidation-reaction product obtained by allowing $\alpha$ acid (humulones), $\beta$ acid (lupulones), iso $\alpha$ acid (isohumulones) and the like in a hop extract to undergo an oxidation-reaction to reduce the contents thereof has a lipid absorption suppressing effect as a health functional effect in spite of significantly receded contents of iso $\alpha$ acid and the like, and the hop extract oxidation-reaction product has significantly reduced bitter and harsh tastes. Further, the present inventors find that the hop extract oxidation-reaction product can be efficiently prepared by powderizing a hop extract followed by exposure to oxygen. The present invention is based on these findings.

That is, according to the present invention, provided is a method of preparing a hop extract oxidation-reaction product, the method comprising: oxidizing a powdered hop extract comprising a hop extract and a base material for powdering.

According to the present invention, also provided are a hop extract oxidation-reaction product having reduced bitter and harsh tastes prepared according to the method described above (hereinafter may be called "the hop extract oxidation-reaction product of the present invention") and food and drink comprising the hop extract oxidation-reaction product (hereinafter may be called "the food and drink of the present invention").

According to the present invention, further provided is a lipid absorption suppressing agent comprising the hop extract oxidation-reaction product as an active ingredient (hereinafter may be called "the suppressing agent of the present invention").

According to the present invention, further provided is a method of suppressing lipid absorption, the method comprising: administering the hop extract oxidation-reaction product to a mammal including human.

According to the present invention, provided is the use of the hop extract oxidation-reaction product in manufacture of food and drink having a lipid absorption suppressing effect.

The hop extract oxidation-reaction product of the present invention has a lipid absorption suppressing effect, but has neither an intense bitter taste as in an isomerized hop extract nor an intense harsh taste as in a non isomerized hop extract. Therefore, the hop extract oxidation-reaction product of the present invention and the suppressing agent of the present invention are advantageous in that they can be ingested as it is without subjecting to a means of masking bitter and harsh tastes while expecting a physiological activity such as a lipid absorption suppressing effect.

BRIEF DESCRIPTION OF THE DRAWINGS

FIG. 2-1 shows a HPLC chromatogram (detection wavelength: 270 nm) of an oxidation-reaction product (Example 1) after a hop extract prepared by supercritical carbon dioxide extraction was powdered and then subjected to an oxidation-reaction.

FIG. 2-2 shows an enlarged view of the HPLC chromatogram (detection wavelength: 270 nm) of an oxidation-reaction product (Example 1) after a hop extract prepared by supercritical carbon dioxide extraction was powdered and then subjected to an oxidation-reaction.

FIG. 2-3 shows another enlarged view of the HPLC chromatogram (detection wavelength: 270 nm) of an oxidation-reaction product (Example 1) after a hop extract prepared by supercritical carbon dioxide extraction was powdered and then subjected to an oxidation-reaction.

FIG. 2-4 shows a HPLC chromatogram (detection wavelength: 355 nm) of an oxidation-reaction product (Example 1) after a hop extract prepared by supercritical carbon dioxide extraction was powdered and then subjected to an oxidation-reaction.

FIG. 3-1 shows a HPLC chromatogram (detection wavelength: 270 nm) of a hop extract which is a raw material for preparing the hop extract oxidation-reaction product of Example 1.

FIG. 3-2 shows an enlarged view of the HPLC chromatogram (detection wavelength: 270 nm) of a hop extract which is a raw material for preparing the hop extract oxidation-reaction product of Example 1.

FIG. 3-3 shows an enlarged view of the HPLC chromatogram (detection wavelength: 355 nm) of a hop extract which is a raw material for preparing the hop extract oxidation-reaction product of Example 1.

FIG. 4-1 shows a HPLC chromatogram (detection wavelength: 270 nm) of an oxidation-reaction product (Example 2) after a hop extract prepared by supercritical carbon dioxide extraction was powdered and then subjected to an oxidation-reaction.

FIG. 4-2 shows an enlarged view of the HPLC chromatogram (detection wavelength: 270 nm) of an oxidation-reaction product (Example 2) after a hop extract prepared by supercritical carbon dioxide extraction was powdered and then subjected to an oxidation-reaction.

FIG. 4-3 shows another enlarged view of the HPLC chromatogram (detection wavelength: 270 nm) of an oxidation-reaction product (Example 2) after a hop extract prepared by supercritical carbon dioxide extraction was powdered and then subjected to an oxidation-reaction.

FIG. 4-4 shows a HPLC chromatogram (detection wavelength: 355 nm) of an oxidation-reaction product (Example 2) after a hop extract prepared by supercritical carbon dioxide extraction was powdered and then subjected to an oxidation-reaction.

FIG. 5-1 shows a HPLC chromatogram (detection wavelength: 270 nm) of a hop extract which is a raw material for preparing the hop extract oxidation-reaction product of Example 2.

FIG. 5-2 shows an enlarged view of the HPLC chromatogram (detection wavelength: 270 nm) of a hop extract which is a raw material for preparing the hop extract oxidation-reaction product of Example 2.

FIG. 5-3 shows a HPLC chromatogram (detection wavelength: 355 nm) of a hop extract which is a raw material for preparing the hop extract oxidation-reaction product of Example 2.

FIG. 6-1 shows a HPLC chromatogram (detection wavelength: 270 nm) of an oxidation-reaction product (Example 3) after a hop extract prepared by performing supercritical carbon dioxide extraction and then isomerization treatment was powdered and then subjected to an oxidation-reaction.

FIG. 6-2 shows an enlarged view of the HPLC chromatogram (detection wavelength: 270 nm) of an oxidation-reaction product (Example 3) after a hop extract prepared by performing supercritical carbon dioxide extraction and then isomerization treatment was powdered and then subjected to an oxidation-reaction.

FIG. 6-3 shows another enlarged view of the HPLC chromatogram (detection wavelength: 270 nm) of an oxidation-reaction product (Example 3) after a hop extract prepared by performing supercritical carbon dioxide extraction and then isomerization treatment was powdered and then subjected to an oxidation-reaction.

FIG. 6-4 shows a HPLC chromatogram (detection wavelength: 355 nm) of an oxidation-reaction product (Example 3) after a hop extract prepared by performing supercritical carbon dioxide extraction and then isomerization treatment was powdered and then subjected to an oxidation-reaction.

FIG. 7-1 shows a HPLC chromatogram (detection wavelength: 270 nm) of a hop extract which is a raw material for preparing the hop extract oxidation-reaction product of Example 3.

FIG. 7-2 shows an enlarged view of the HPLC chromatogram (detection wavelength: 270 nm) of a hop extract which is a raw material for preparing the hop extract oxidation-reaction product of Example 3.

FIG. 7-3 shows a HPLC chromatogram (detection wavelength: 355 nm) of a hop extract which is a raw material for preparing the hop extract oxidation-reaction product of Example 3.

FIG. 8-1 shows HPLC chromatograms (detection wavelength: 270 nm) of the raw hop extract of Example 5 and the hop extract oxidation-reaction product after subjected to an oxidation-reaction at 60° C. for 24 hours.

FIG. 8-2 shows an enlarged view of the HPLC chromatograms (detection wavelength: 270 nm) of the raw hop extract of Example 5 and the hop extract oxidation-reaction product after subjected to an oxidation-reaction at 60° C. for 24 hours.

FIG. 8-3 shows a HPLC chromatogram (detection wavelength: 270 nm) of the hop extract oxidation-reaction product of Example 7.

FIG. 8-4 shows a HPLC chromatogram (detection wavelength: 270 nm) of the hop extract oxidation-reaction product of Example 8.

FIG. 8-5 shows a HPLC chromatogram (detection wavelength: 270 nm) of the hop extract oxidation-reaction product of Example 9.

FIG. 8-6 shows a HPLC chromatogram (detection wavelength: 270 nm) of the hop extract oxidation-reaction product of Example 10.

FIG. 8-7 shows a HPLC chromatogram (detection wavelength: 270 nm) of the hop extract oxidation-reaction product of Example 11.

FIG. 8-8 shows a HPLC chromatogram (detection wavelength: 270 nm) of the hop extract oxidation-reaction product of Example 12.

FIG. 11 shows a 50% pancreatic lipase activity inhibitory concentration (IC50) of a hop extract oxidation-reaction product.

DETAILED DESCRIPTION OF THE INVENTION

HOP Extract Oxidation-Reaction Product

Figure 1:
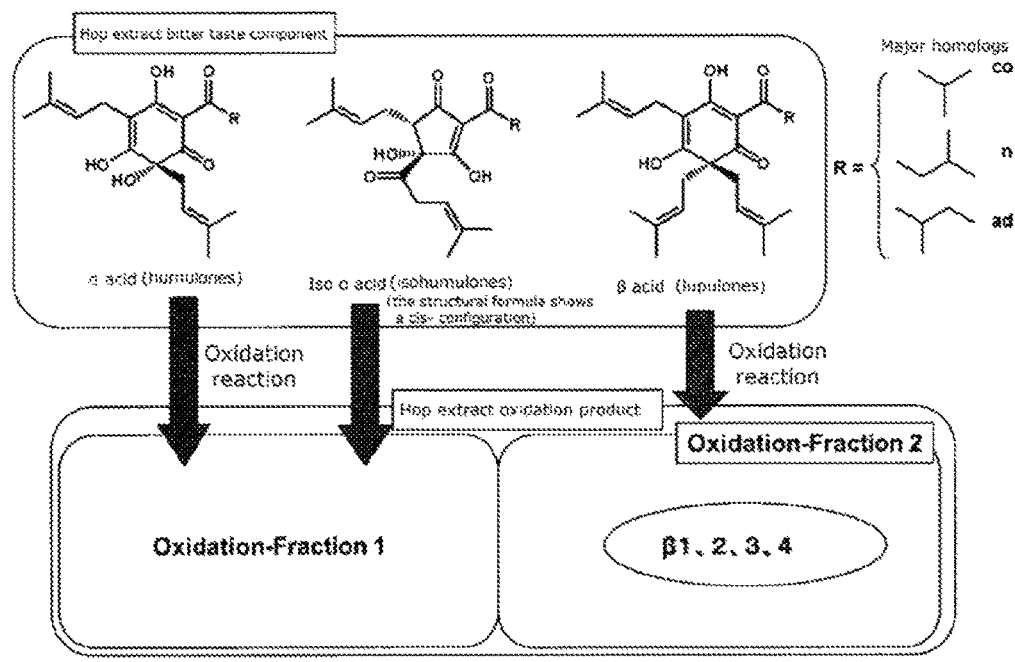
FIG. 1 shows bitter taste components contained in a hop extract, and components contained in a hop extract oxidation-reaction product.

The hop extract oxidation-reaction product provided according to the present invention can be obtained by subjecting components in a hop extract to an oxidation-reaction. There is no particular limitation for an "oxidation-reaction" in the present invention, as long as α acid, iso α acid and β acid which are components in a hop extract can be transformed into a more hydrophilic oxidation-reaction product. Note that a progress of the reaction can be monitored by HPLC analysis. Further, the term "hop extract" as used in the present invention means an extract of hop cone. The term is used to encompass an isomerized hop extract obtained by subjecting a hop extract to isomerization treatment and a reduced isomerized hop extract obtained by reducing iso α acid using a reducing agent. An extraction method and isomerization treatment of a hop extract will be described below.

A hop extract contains acidic resin components such as α acid (humulones) and β acid (lupulones), while an isomerized hop extract contains acidic resin components such as iso α acid (isohumulones). The terms "α acid, humulones" as used in the present invention are meant to include humulone, adhumulone, cohumulone, post-humulone and pre-humulone. Further, the terms "β acid, lupulones" as used in the present invention are meant to include lupulone, adlupulone, colupulone, post-lupulone and pre-lupulone. Moreover, the terms "iso α acid, isohumulones" as used in the present invention are meant to include isohumulone, isoadhumulone, isocohumulone, isoposthumulone, Isoprehumulone, Rho-isohumulone, Rho-isoadhumulone, Rho-isocohumulone, Rho-isoposthumulone, Rho-isoprehumulone, tetrahydro isohumulone, tetrahydro isoadhumulone, tetrahydro isocohumulone, tetrahydro isoprehumulone, tetrahydro isoposthumulone, hexahydro isohumulone, hexahydro isoadhumulone, hexahydro isocohumulone, hexahydro isoposthumulone and hexahydro isoprehumulone. Note that isohumulones are present in both cis and trans stereoisomers. Unless otherwise stated, the term is meant to include the both. In the present invention, the components described above may also be collectively called bitter taste components.

As described above, there are various types of hop extracts. The conventional uses of hop extracts are almost limited to brewing of beer type drinks and non-alcohol beer tasted drinks. They are used mainly for the purposes of conferring beer-like bitter tastes and flavors on these drinks. A hop extract shows better storage stability as compared with original plant articles such as a hop cone and hop pellet, and bitter taste components contained therein also show good stability and good homogeneity. Therefore, the hop extract can stably provide the bitter taste components with the drinks described above. In this context, the idea that a hop extract is used after intentionally subjected to an oxidation-reaction to reduce bitter taste components such as α acid, β acid and iso α acid is unprecedented. Further, since the bitter taste components in an extract are more stable than in original plant articles, it is difficult to efficiently obtain an oxidation-reaction product when they are directly subjected to an oxidation-reaction. In contrast, when a hop extract is first powderized and then subjected to an oxidation-reaction, the hop extract oxidation product of the present invention can be obtained very efficiently.

According to Examples described below, by subjecting a hop extract to an oxidation-reaction, the contents of α acid, iso α acid and β acid are reduced while the contents of these components such as oxidation-fraction 1 (Oxi-Fr1), oxidation-fraction 2 (Oxi-Fr2), β1, β2, β3 and β4 are increased (see Example 4 for the analytical method and the definitions of these components). Therefore, Examples of the "hop extract oxidation-reaction product" include hop extract oxidation-reaction products in which "Oxi-Fr1/(α acid+iso α acid)" is 0.1 or more by weight ratio, or "(β1+β2+β3+β4)/β acid" is 0.3 or more by weight ratio, or "Oxi-Fr2/β acid" is 2.0 or more by weight ratio as determined by the HPLC analysis of Example 4 (β1+β2+β3+β4 is also termed as β1-4). Note that a raw hop extract in which the content of either (α acid+iso α acid) or β acid is negligible as compared with the content of the other (roughly speaking, 1/10 or less) can be used. In this case, a parameter for the component of the negligible content can be disregarded among the parameters described above (for example, Examples 2 and 10).

Further, as clearly seen from Example 2, Oxi-Fr2 comprising each component of β1-4 mainly comprises oxidation-reaction products of β acid in a hop extract. This finding and Examples 10 and 12 reveal that Oxi-Fr1 mainly comprises oxidation-reaction products of α acid and iso α acid in a hop extract. FIG. 1 shows a relationship between the bitter taste components in a hop extract and the oxidation-reaction products.

Further, as clearly seen from Example 17, each component of β1-4 comprises compounds shown below.

β1

β1 comprises any of the compounds represented by the following formula (I). β1 may be any one of the compounds represented by the formula (I), or may be a mixture of the compounds represented by the formula (I). Therefore, according to one aspect, β1 is one of the compounds represented by the formula (I) or the both.

[Formula 1]

Formula (I)

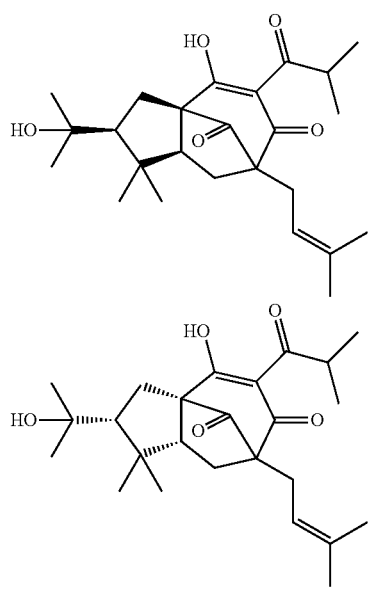

β2

β2 comprises any of the compounds represented by the following formula (II). β2 may be any one of the compounds represented by the formula (II), or may be a mixture of the compounds represented by the formula (II). Therefore, according to one aspect, β2 is one of the compounds represented by the formula (II) or the both.

[Formula 2]

Formula (II)

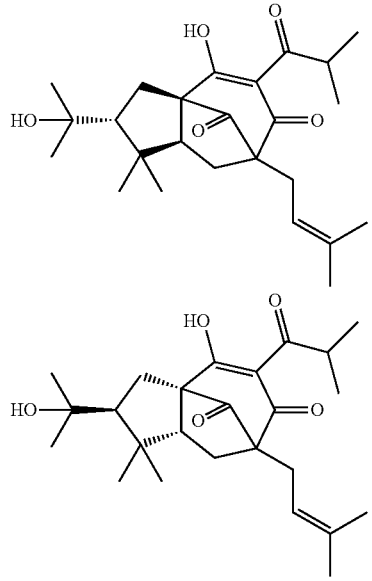

β3

β3 comprises any of the compounds represented by the following formula (III) or (IV). β3 may be any one of the compounds represented by the formula (III) or (IV), or may be a mixture of any two or more compounds represented by the formula (III) or (IV). Therefore, according to one aspect, β2 is at least one compound selected from the compounds represented by the formula (III) and the compounds represented by the formula (IV).

[Formula 3]

Formula (III)

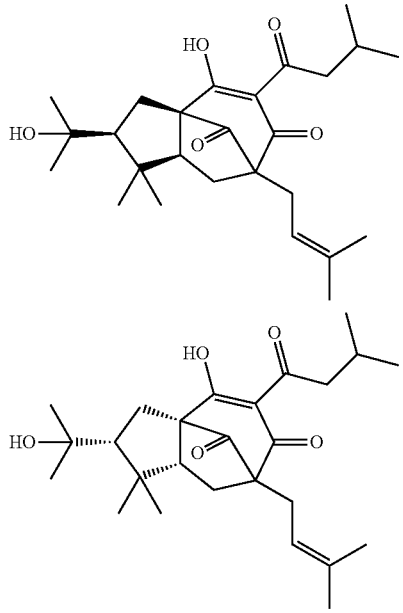

[Formula 4]

Formula (IV)

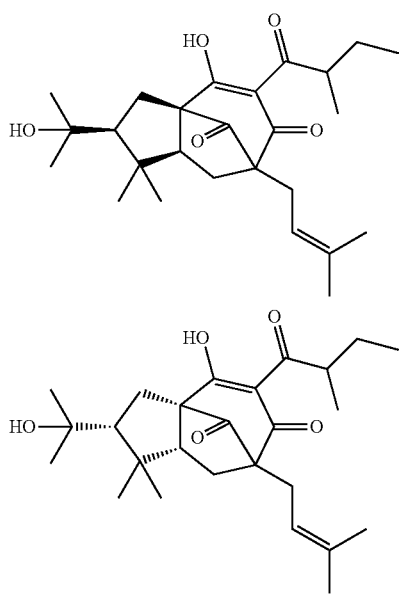

β4

β4 comprises any of the compounds represented by the following formula (V) and (VI). β4 may be any one of the compounds represented by the formula (V) or (VI), or may be a mixture of any two or more compounds represented by the formula (V) or (VI). Therefore, according to one aspect, β4 is at least one compound selected from the compounds represented by the formula (V) and the compounds represented by the formula (VI).

[Formula 5]

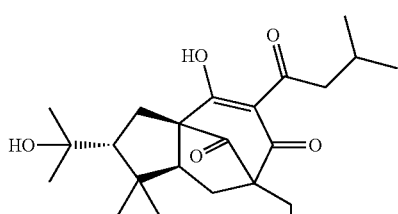

Formula (V)

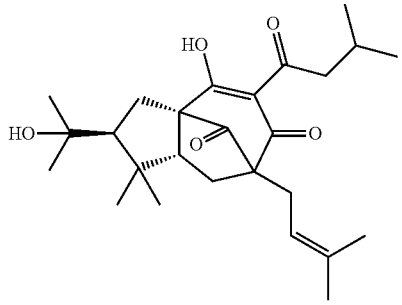

[Formula 6]

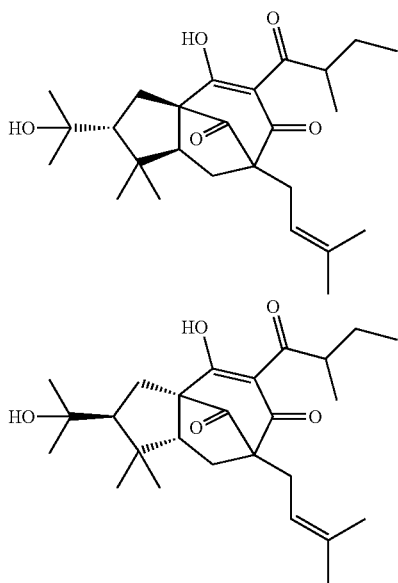

Formula (VI)

The hop extract oxidation-reaction products prepared according to the procedures described in Examples 1 to 3 and 5 to 12 contain oxidation-reaction products of α acid, β acid and iso α acid. As shown in Example 13, the hop extract oxidation-reaction product having the oxidation-reaction products as a main component shows reduced bitter and harsh tastes characteristic of a hop extract, and can show a physiological activity as shown in Examples 14 and 15.

Preparation of a Hop Extract Oxidation-Reaction Product Oxidation-Reaction after Powderization Treatment The hop extract oxidation-reaction product of the present invention can be efficiently prepared by mixing a hop extract with a base material for powdering to perform powderization followed by an oxidation-reaction. Considering that an oxidation-reaction requires enormously long time in the case of heating a hop extract as it is, performing oxidization after powderization of a hop extract as in the present invention is industrially advantageous.

With regards to powderization of a hop extract, there is no particular limitation for a weight ratio of a hop extract and a base material for powdering as long as a powdered hop extract can be homogeneously prepared, but the ratio is preferably about 1:1 to 1:10, more preferably about 1:2 to 1:5.

Further, the range of temperature for an oxidation-reaction of a hop extract is preferably between room temperature and 120° C., more preferably 60° C. to 80° C.

Moreover, the reaction time for an oxidation-reaction of a hop extract is preferably several hours to several weeks, more preferably 4 hours to one week, even more preferably 8 hours to 96 hours.

There is no particular limitation for a base material for powdering as long as it can be used for powdering a hop extract, but an additive acceptable as general food as well as food and drink itself are preferred, considering that a hop extract oxidation-reaction product is to be used for a food product. Such additives and food products are preferably polysaccharides, inorganic carriers and brewing raw materials. More preferably, they include excipients such as dextrin and cellulose; preparing auxiliary agents such as diatomaceous earth, perlite and activated earth; and a food product such as hop and hop lees. For a base material for powdering, a single base material may be used or a mixture comprising two or more base materials at any ratio may be used. Further, a powdered hop extract oxidation-reaction product after subjected to an oxidation-reaction may be used as it is, but the base material used for powdering may be removed to use hop extract oxidation-reaction components only. In order to extract hop extract oxidation-reaction components only, the hop extract components may be dissolved in a solvent in which the base material is not dissolved. For example, in a case where dextrin is used for a base material, a solvent such as ethanol can be used. In a case where cellulose is used for a base material, a solvent such as ethanol and an alkaline aqueous solution can be used to extract hop oxidation-reaction components only. In a case where a base material used for powdering does not need to be separated, the base material may be formulated together. Alternatively, the solvent used for formulation may be removed, and a dried form may be used.

An oxidation-reaction reduces α acid, iso α acid and β acid which are contained in a hop extract. The degree of decrease in these components can be analyzed and determined by HPLC and the like. A proportion of the peak area of iso α acid, α acid and β acid to the total peak area of components detected with a wavelength of 270 nm as determined by HPLC analysis of a hop extract oxidation-reaction product is preferably 50% or less, more preferably 30% or less, even more preferably 10% or less. Therefore, according to one aspect of the present invention, a hop extract oxidation-reaction product is provided in which a proportion of the peak area of iso α acid, α acid and β acid to the total peak area of the hop extract oxidation-reaction product as determined by HPLC analysis is 50% or less.

For example, a hop extract used as a raw material for preparing the hop extract oxidation-reaction product of the present invention can be prepared by subjecting hop cone and compressed matter thereof to an extraction operation after grinding or as it is. Extraction methods include, for example, an extraction method with an ethanol solvent which is used for a method of preparing a hop extract used in brewing beer and the supercritical carbon dioxide extraction method. Among these, the supercritical carbon dioxide extraction has a characteristic where bitter taste components and essential oil components are more enriched with less polyphenols components. Further, other commonly used methods can be employed as hop extraction methods, including, for example, a method of insuccation in which hop cone, ground products thereof and the like are subjected to cold or warm maceration in a solvent; and a method in which extraction is performed with stirring and heading, and an extracted liquid is obtained after filtering; the percolation method or the like. After removing solid materials by filtration or centrifugation if desired, an extracted liquid obtained may be used as it is or may be used as a partly concentrated or dried form after removing a solvent depending on embodiments of use. Further, after concentrating or drying, it may be used after further washed and purified with a non-dissolving solvent or may be used after further dissolving or suspending in a suitable solvent. Moreover, a dried hop extract can be used which is obtained by drying the extracted liquid obtained as described above with a conventional means such as reduced pressure drying, lyophilization and the like.

Solvent used for the extraction described above include, for example, water; lower alcohols having 1 to 4 carbon atoms such as methanol, ethanol, propanol and butanol; lower alkyl esters such as acetic acid ethyl ester; glycols such as ethylene glycol, butylene glycol, propylene glycol and glycerin; in addition to this, polar solvents such as acetone and acetic acid; hydrocarbons such as benzene and hexane; known organic nonpolar solvents such as ethers such as ethyl ether and petroleum ether. These solvents may be used alone or in combination of two or more.

For a hop extract used as a raw material for preparing the hop extract oxidation-reaction product of the present invention, an isomerized hop extract obtained by further subjecting the hop extract described above to isomerization treatment, and a reduced and isomerized hop extract obtained by reducing iso α acid with a reducing agent may be used. Methods of isomerization treatment are known and any of them may be used, but typically, the isomerization treatment can be performed by heating a hop extract under a weakly alkaline condition of pH 8 to 9 or in the presence of magnesium oxide. A hop extract may be subjected to isomerization treatment as it is, but prior to isomerization treatment, a hop extract may be added to heated alkaline water (pH 8 to 9 after adding the hop extract), dissolved α acid and insoluble β acid may be separated, and then the resulting α acid fraction may be subjected to isomerization treatment.

Hop extracts to be used for preparing a hop extract oxidation-reaction product are commercially available as beer additives, and a commercially available product can be used in the present invention. For example, the followings can be used: a hop extract in which humulones and lupulones are mainly extracted from ground products of hop cone by supercritical carbon dioxide extraction (for example, $CO_2$ Hop Extract (Hopsteiner)), a hop extract in which humulones and lupulones are mainly extracted from ground products of hop cone by ethanol extraction (for example, Ethanol Hop Extract (Hopsteiner)), a hop extract in which lupulones are mainly extracted from ground products of hop cone by supercritical carbon dioxide extraction (for example, Beta Aroma Extract (Hopsteiner)), an extract in which an extract of ground products of hop cone by carbon dioxide gas is isomerized (for example, Isomerized Kettle Extract (Hopsteiner)), an extract in which an extract of ground products of hop cone by carbon dioxide gas is isomerized and reduced (for example, Light Stable Kettle Extract (Hopsteiner), Tetra Concentrate (Hopsteiner) and Hexa IsoExtract (Hopsteiner)), a water-soluble extract in which an extract of ground products of hop cone by carbon dioxide gas is isomerized and then further allowed to form potassium salts to produce a low viscous liquid (for example, IsoExtract 30% (Hopsteiner)) and the like. Some of the commercially available hop extracts described above have bitter taste components which are in a form of potassium salts. But for oxidation-reaction, preferred is a hop extract which is present as a resinoid extract of a free form after acid treatment. A fraction containing only a specific bitter taste component in an extract can be used.

Preparation of Alkaline Metal Salts.

The hop extract oxidation-reaction product of the present invention can allow an alkaline metal to form a salt to give an aqueous solution of alkaline metal salts. The aqueous solution can be further powderized by spray dry and the like. Alkaline metal salts which can be used for forming metal salts of the hop extract oxidation-reaction product of the present invention include those salts acceptable for addition to a food product such as potassium salts and sodium salts. The alkaline metal salts of the hop extract oxidation-reaction product of the present invention have good water solubility, which is advantageous in that addition to a food product (in particular to a drink) can be easily performed.

The hop extract oxidation-reaction product of the present invention obtained as described above may be further subjected to fractionation treatment and the like to enrich a specific component in the hop extract oxidation-reaction product. The enriched product also may be added to a food product, or used as the lipid absorption suppressing agent of the present invention.

Applications of Hop Extract Oxidation-Reaction Products

The hop extract oxidation-reaction product has a lipid absorption suppressing effect as shown in Examples 14 to 15 as described below.

Therefore, the hop extract oxidation-reaction product of the present invention is useful as a lipid absorption suppressing agent. The hop extract oxidation-reaction product of the present invention is also useful for preventing and/or treating obesity.

The hop extract oxidation-reaction product of the present invention has neither an intense bitter taste as in an isomerized hop extract nor an intense harsh taste as in a non-isomerized hop extract (Example 13). Therefore, the hop extract oxidation-reaction product of the present invention is advantageous in that it can be used as it is in food and drink or pharmaceutical products without subjecting to a means of masking bitter and harsh tastes while it is expected to show a physiological activity as described above.

Pharmaceutical Products and Food Products

In a case where the hop extract oxidation-reaction product of the present invention is provided as a pharmaceutical product, the pharmaceutical product can be prepared by mixing the hop extract oxidation-reaction product of the present invention with a pharmaceutically acceptable additive. Because the hop extract oxidation-reaction product of the present invention has neither an intense bitter taste as in an isomerized hop extract nor an intense harsh taste as in a non-isomerized hop extract, it is advantageous in that it can be formulated without subjecting to a means of masking bitter and harsh tastes or in a condition where bitter and harsh tastes are fully masked using an existing masking means while it is expected to show a predetermined effect.

In the present invention, not only the hop extract oxidation-reaction product itself but also an isolated or purified specific component contained in the hop extract oxidation-reaction product can be used.

The hop extract oxidation-reaction product of the present invention can be administered orally or parenterally as an active ingredient, and oral administration is preferred. Oral preparations include granule, powder, tablet (including sugar coated tablet), pill, capsule, syrups, emulsion and suspension. Parenteral preparations include injectables (for example, subcutaneous injectables, intravenous injectables, intramuscular injectables, intraperitoneal injectables), drops, external preparations (for example, formulations for transnasal administration, transdermal formulations, ointment) and suppository (for example, rectal suppository, vagina suppository). These pharmaceutical preparations can be formulated using a pharmaceutically acceptable carrier by an approach usually performed in the art. Pharmaceutically acceptable carriers include excipients, binders, diluents, additives, flavoring agents, buffers, thickeners, colorants, stabilizers, emulsifying agents, dispersing agents, suspending agents and antiseptic agents. For example, the followings can be used as a carrier: magnesium carbonate, magnesium stearate, talc, sugar, lactose, pectin, dextrin, starch, gelatin, tragacanth, methyl cellulose, sodium carboxymethylcellulose, low melting point wax and cacao butter.

For example, a pharmaceutical preparation can be prepared as follows. An oral preparation can be prepared by adding, for example, an excipient (for example, lactose, white soft sugar, starch, Mannitol), a disintegrator (for example, calcium carbonate, carboxymethylcellulose calcium), a binder (for example, pregelatinized starch, gum arabic, carboxymethylcellulose, polyvinylpyrrolidone, hydroxypropylcellulose), or a lubricant (for example, talc, magnesium stearate, polyethylene glycol 6000) to an active ingredient, performing compression molding, and then if desired, performing coating by a publicly acknowledged method for the purposes of masking tastes, enteric-coating, or prolonged duration. For coating agents, the followings can be used: for example ethylcellulose, hydroxymethylcellulose, polyoxyethylene glycol, cellulose acetate phthalate, hydroxypropylmethylcellulose phthalate and EUDRAGIT (Röhm Pharma GmbH, Germany, methacrylic acid-acrylic acid copolymer).

An injectable can be prepared by dissolving, suspending or emulsifying an active ingredient in an aqueous solvent (for example, distilled water, physiological saline, Ringer's solution and the like) or an oleaginous solvent (for example, vegetable oils such as olive oil, sesame oil, cotton seed oil and corn oil; propylene glycol) or the like along with a dispersing agent (for example, Tween 80 (Atlas Powder Co., U.S.), HCO60 (Nikko Chemicals Co., Ltd.), polyethylene glycol, carboxymethylcellulose, sodium alginate and the like), a preservative (for example, methylparaben, propylparaben, benzyl alcohol, chlorobutanol, phenol), an isotonizing agent (for example, sodium chloride, glycerin, sorbitol, glucose, invert sugar) and the like. In that case, an additive such as a solubilizing agent (for example, sodium salicylate, sodium acetate), a stabilizer (for example, human serum albumin) and a soothing agent (for example, benzalkonium chloride, procaine hydrochloride) may be added if desired.

An external preparation can be prepared by transforming an active ingredient to a solid, semi-solid, or liquid composition. For example, the solid composition can be prepared by powdering an active ingredient as it is or powdering an active ingredient to which added and mixed are an excipient (for example, lactose, mannitol, starch, microcrystalline cellulose and white soft sugar), a thickener (for example, natural gums, cellulose derivatives, acrylic acid polymer) and the like. The liquid composition can be prepared in the almost same way as injectables. The semi-solid composition is preferably an aqueous or oleaginous gel or a cartilage-like substance. Further, each of these compositions may contain a pH regulator (for example, carbonic acid, phosphoric acid, citric acid, hydrochloric acid, sodium hydroxide), an antiseptic agent (for example, parahydroxybenzoate esters, chlorobutanol, benzalkonium chloride) and the like. Suppository can be prepared by transforming an active ingredient to an oleaginous or aqueous solid, semi-solid, or liquid composition. Oleaginous bases used for the composition include glycerides of higher fatty acids [for example, cacao butter, witepsols (Dynamit Nobel GmbH)], middle fatty acids [for example, migriols (Dynamit Nobel GmbH)] or vegetable oils (for example, sesame oil, soybean oil, cotton seed oil). Aqueous bases include polyethylene glycols and propylene glycol. Further, aqueous gel bases include natural gums, cellulose derivatives, vinyl polymers and acrylic acid polymers.

The hop extract oxidation-reaction product of the present invention can be used for addition to food and drink. The hop extract oxidation-reaction product of the present invention demonstrates a physiological activity such as a lipid absorption suppressing effect as described above. Therefore, a physiological activity such as a lipid absorption suppressing effect is expected from the food and drink to which the hop extract oxidation-reaction product of the present invention is added.

The food and drink of the present invention is food and drink containing an effective amount of the hop extract oxidation-reaction product of the present invention.

The phrase "containing an effective amount" of the hop extract oxidation-reaction product of the present invention as used herein means a content in which the hop extract oxidation-reaction product is to be ingested in the range as described below when individual food and drink is consumed in a commonly consumed amount.

In a case where the hop extract oxidation-reaction product of the present invention is provided as food and drink, the hop extract oxidation-reaction product of the present invention can be included into food and drink as it is. More specifically, the food and drink of the present invention can be those in which the hop extract oxidation-reaction product of the present invention is prepared as food and drink as it is; those to which various proteins, saccharides, lipids, trace elements, vitamins and the like are further added; those transformed into a liquid, semi-liquid or solid; those transformed into an aqueous solution of potassium salts, sodium salts and the like; and those added to general food and drink. Because the hop extract oxidation-reaction product of the present invention has neither an intense bitter taste as in an isomerized hop extract nor an intense harsh taste as in a non-isomerized hop extract, it is advantageous in that it can be made into food and drink without subjecting to a means of masking bitter and harsh tastes or in a condition where bitter and harsh tastes are fully masked using an existing masking means while it is expected to show a predetermined effect.

The term "food and drink" as used in the present invention is meant to include health food, functional food, food for specified health use and food for the sick.

Further, a form of "food and drink" may not be particularly limited, for example, may be a form of a drink.

The hop extract oxidation-reaction product of the present invention can be provided as food and drink which is useful for maintenance and promotion of good health, specifically as food and drink having a function such as a lipid absorption suppressing effect by including the hop extract oxidation-reaction product of the present invention to food and drink for daily ingestion, health food and functional food taken as a supplement, preferably lipid-containing food, high-calorie food and the like because the hop extract oxidation-reaction product of the present invention has a lipid absorption suppressing effect. That is, the food product of the present invention can be provided as food and drink, in particular food for specified health use suitable for consumers who are conscious of high fat plasma and accumulation of fat (in particular, accumulation of body fat and visceral fat) and consumers who are conscious of weight gain.

Specifically, examples of such food and drink include, but not limited to, carbohydrate-containing food and drink such as rice food, noodles, bread and pasta; western confectionery such as cookie and cake; Japanese confectionery such as a bun with a bean-jam filling and sweet bean jelly; candy; gum; various confectionaries such as cooled or iced confectionary such as yogurt and pudding; alcoholic beverages such as whiskey, bourbon, spirits, liqueur, wine, fruit wine, sake, Chinese liquor, shochu, beer, non-alcohol beer having 1% or less alcohol content, low-malt beer, other miscellaneous liquors and shochu highball; non-alcoholic beverages such as a drink containing fruit juice, a drink containing vegetable juice, a drink containing fruit juice and vegetable juice, soft drink, milk, soybean milk, milk beverages, drinkable yogurt, drinkable jelly, coffee, cocoa, tea drink, energy drink, sports drink and mineral water; processed products in which eggs are used, processed products of fish (squid, octopus, shellfish, eel and the like) and meat (including giblets such as lever) (including rare delicacy) and the like.

Tea drinks include, for example, black tea, green tea, barley tea, brown rice tea, green tea of middle grade, green tea of highest quality, roasted tea, oolong tea, turmeric tea, puer tea, rooibos tea, rose tea, chrysanthemum tea and herbal tea (for example, mint tea, jasmine tea).

Fruits used for the drink containing fruit juice and the drink containing fruit juice and vegetable juice include, for example, apple, mandarin orange, grape, banana, pear and plum. Further, vegetables used for the drink containing vegetable juice or the drink containing fruit juice and vegetable juice include, for example, tomato, carrot, celery, cucumber and watermelon.

The pharmaceutical product and food and drink of the present invention, which use a hop extract that human beings have taken in as food and drink for many years, show low toxicity, and can be used safely to mammals in need thereof (for example, human, mouse, rat, rabbit, canine, feline, bovine, equine, swine, monkey and the like). The dosage or intake of the hop extract oxidation-reaction product of the present invention can be determined depending on recipient, age and weight of recipient, conditions, administration time, a dosage form, a mode of administration and a combination of medicaments and the like. For example, in a case where the hop extract oxidation-reaction product of the present invention is orally administered as a medicine, the hop extract oxidation-reaction product is administered 1 to 3 times a day such that the total amount is in the range of 10 to 600 mg, more preferably 20 to 200 mg per day per 60 Kg of adult weight in terms of isohumulone equivalence, and in the case of parenteral administration, the range is 1 to 100 mg, more preferably 3 to 30 mg. The dosage of a drug having a different mechanism of action which is used in combination of the hop extract oxidation-reaction product of the present invention can also be suitably determined based on the clinically used dosage for each. Further, in a case where the hop extract oxidation-reaction product of the present invention is ingested as food and drink, the hop extract oxidation-reaction product of the present invention can be included into food products such that the total amount of the hop extract oxidation product is in the range of 25 to 9600 mg, more preferably 25 to 780 mg per day per 60 Kg of adult weight in terms of isohumulone equivalence.

EXAMPLES

The present invention is specifically described based on the following examples, but the present invention shall not be limited to these examples.

Example 1

Preparation of a Hop Extract Oxidation-Reaction Product from a Hop Extract Prepared by Supercritical Carbon Dioxide Extraction 1

Sixty grams of a hop extract prepared by supercritical carbon dioxide extraction ($CO_2$ Hop Extract; α acid 55.6% w/w and, β acid 22.6% w/w, iso α acid not detected; Hopsteiner) and 120 g of dextrin (TK-16; Matsutani Chemical Industry Co., Ltd.) were mixed to uniformity in a weight ratio of 1:3, and the hop extract was then powderized. The resulting powdered hop extract was heated at 80° C. for 24 hours for an oxidation-reaction.

Example 2

Preparation of a Hop Extract Oxidation-Reaction Product from a Hop Extract Prepared by Supercritical Carbon Dioxide Extraction 2

Twenty grams of a hop extract prepared by supercritical carbon dioxide extraction (Beta Aroma Extract; β acid 41.3% w/w, α acid and iso α acid not detected; Hopsteiner) and 60 g of dextrin (TK-16; Matsutani Chemical Industry Co., Ltd.) were mixed to uniformity in a weight ratio of 1:3, and the hop extract was then powderized. The resulting powdered hop extract was heated at 80° C. for 24 hours for an oxidation-reaction.

Example 3

Preparation of a Hop Extract Oxidation-Reaction Product from a Hop Extract which was Isomerized after Supercritical Carbon Dioxide Extraction Twenty grams of a hop extract which was isomerized after supercritical carbon dioxide extraction (Isomerized Kettle Extract; iso α acid 53.0% w/w, β acid 20.0% w/w, α acid not detected; Hopsteiner) and 60 g of dextrin (TK-16; Matsutani Chemical Industry Co., Ltd.) were mixed to uniformity in a weight ratio of 1:3, and the hop extract was then powderized. The resulting powdered hop extract was heated at 80° C. for 24 hours for an oxidation-reaction.

Example 4

Analysis of the Hop Extract Oxidation-Reaction Products

The hop extract oxidation-reaction products prepared in Examples 1 to 3 were pre-treated for analysis as described below.

Pretreatment for Analysis

Hop extract components were extracted with ethanol from the powdered hop extract after the reaction, and prepared to give a solid content from the hop extract of 2.5 mg/mL for HPLC analysis. The hop extracts used as raw materials in Examples 1 to 3 were also prepared to give the same concentration of the solid content, and analyzed for comparison.

HPLC System Configuration
Pump: LC-20AD×3 (SHIMADZU CORPORATION)
Degasser: DGU-20A5 (SHIMADZU CORPORATION)
System controller: CBM-20A (SHIMADZU CORPORATION)
Autosampler: SIL-20ACHT (SHIMADZU CORPORATION)
Column oven: CTO-20AC(SHIMADZU CORPORATION)
Photodiode array detector: SPD-M 20A (SHIMADZU CORPORATION)
Waveform analysis software: LCSolution (SHIMADZU CORPORATION)
HPLC Conditions
Column: Alltima C18 2.1 mm I.D.×100 mm, particle diameter 3 μm
Flow rate: 0.6 mL/min
Elution solvent A: water/phosphoric acid, 1000/0.2 (v/v)+ EDTA (free) 0.02% (w/v)
Elution solvent B: acetonitrile
Elution solvent C: water
Injection amount: 3 μL
Column temperature: 40° C.
Detection wavelength: 270 nm (a detection and quantification wavelength for Oxi-Fr1, Oxi-Fr2, iso α acid and β1-4, and a detection wavelength for α acid and β acid): 355 nm (a quantification wavelength for α acid and β acid)
Gradient Program:

TABLE 1

| | Mobile phase composition % | | |
|---|---|---|---|
| Time min | A | B | C |
| 0 | 90 | 10 | 0 |
| 26.67 | 48 | 52 | 0 |
| 30 | 25 | 75 | 0 |
| 32.67 | 15 | 85 | 0 |
| 37.67 | 15 | 85 | 0 |
| 37.68 | 0 | 10 | 90 |
| 41.3 | 0 | 10 | 90 |
| 41.31 | 90 | 10 | 0 |
| 51 | | stop | |

(After 37.68 min. the washing and equilibration step)

Under the above analysis conditions, a group of components which are eluted before iso α acid, specifically trans-isocohumulone and are detectable at 270 nm is designated as Oxidation-Fraction 1 (Oxi-Fr1). Further, a group of components which are eluted before the elution time of α acid, specifically cohumulone uptown the end of the analysis (a time at which a mobile phase in the detector is replaced with a wash solvent) and are detectable at 270 nm, but except for the peaks of α acid and β acid is designated as Oxidation-Fraction 2 (Oxi-Fr2). Furthermore, oxidized compounds contained in Oxi-Fr2, to which one oxygen atom is added to β acid as described below, are designated as β1, β2, β3 and β4. For the waveform analysis, a region where a solvent peak and a negative peak due to an injection shock appear was excluded from the analysis. Calculation of the values of area applied for the quantification analysis of Oxi-Fr1, Oxi-Fr2 and β1-4 is also described below.

Figures 1, 2:
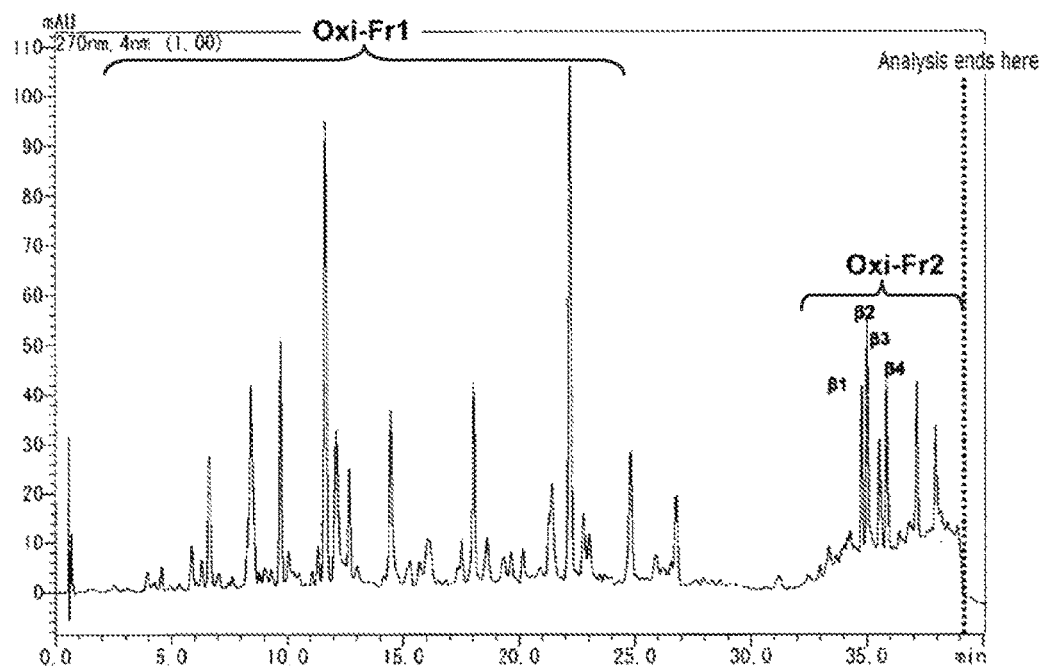
Figure 2:
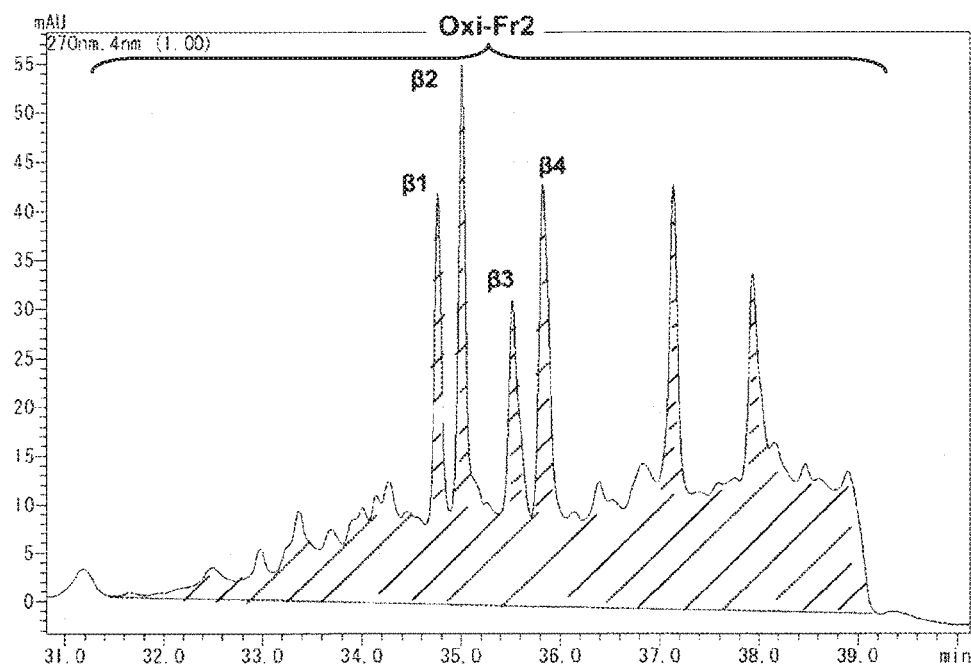
Figures 2, 3:
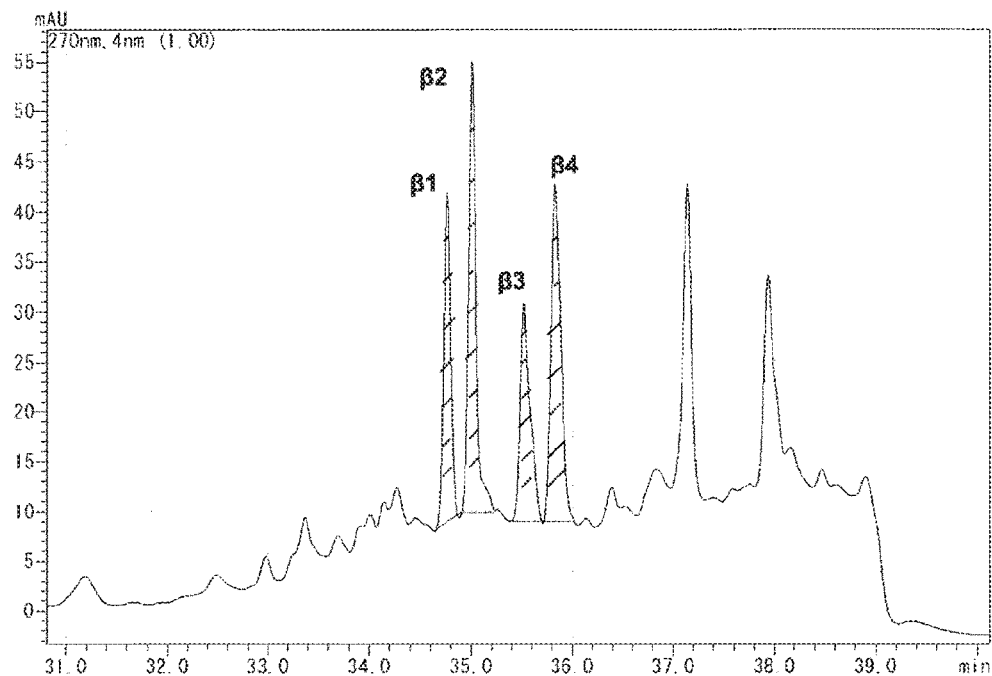
Figures 2, 3, 4:
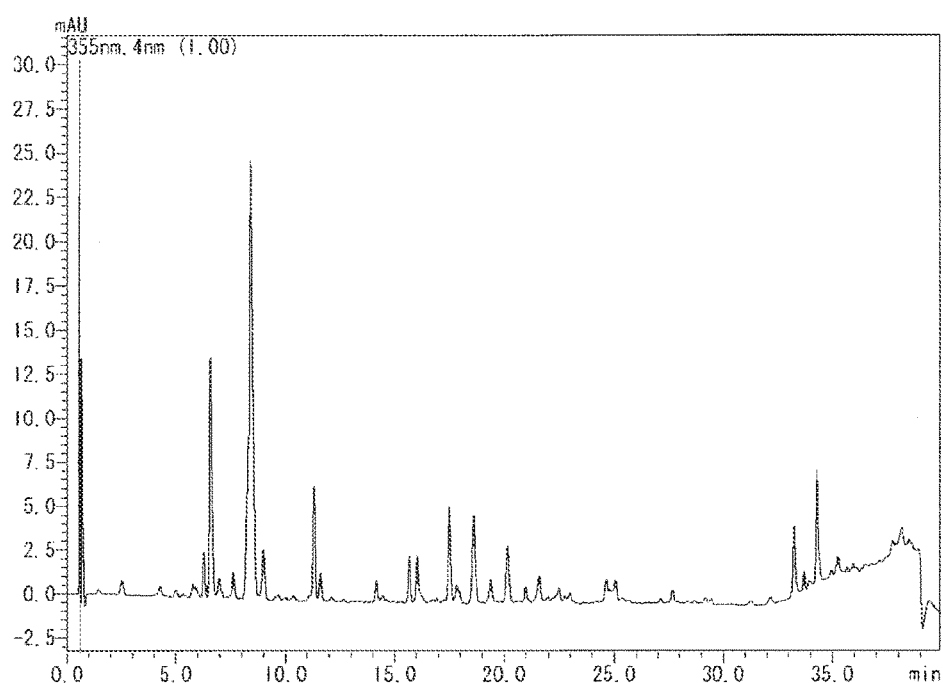
Figures 1, 3:
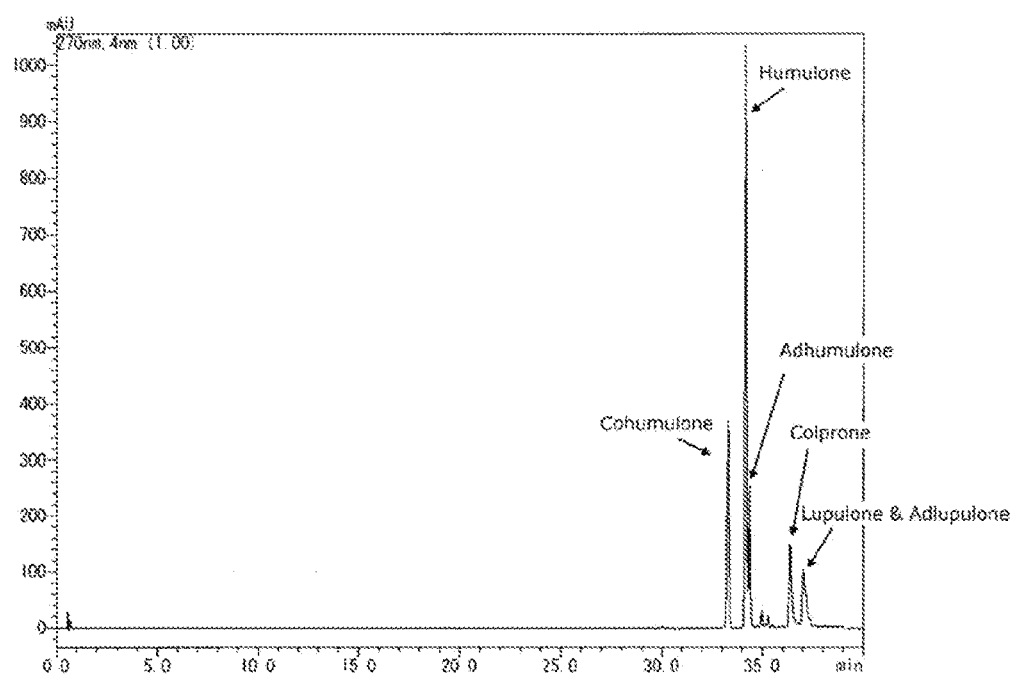
Figures 2, 3:
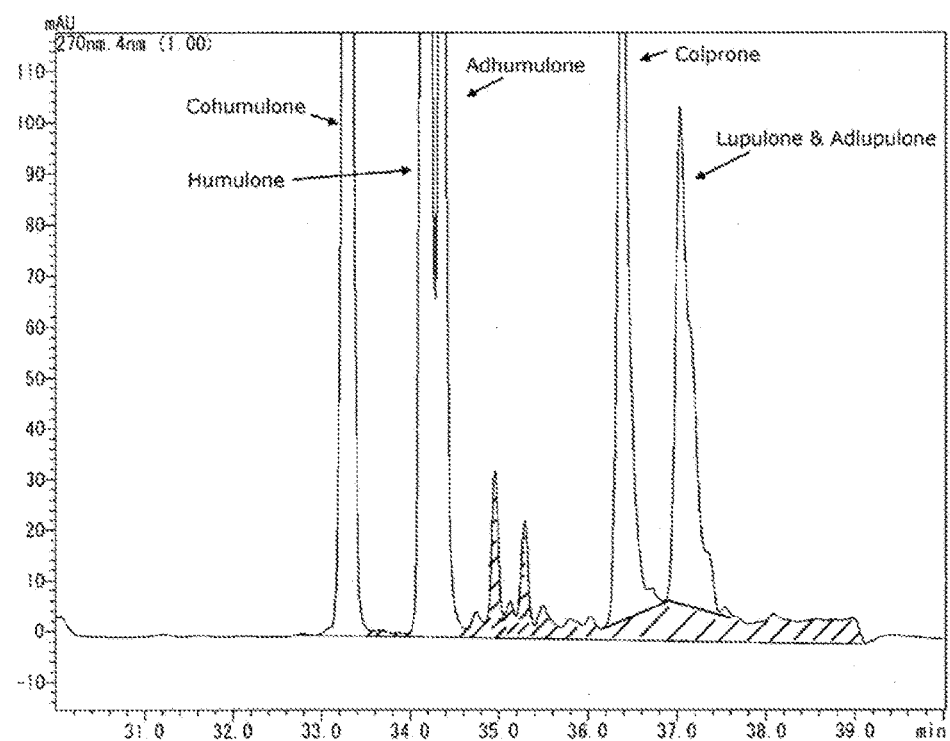
Figure 3:
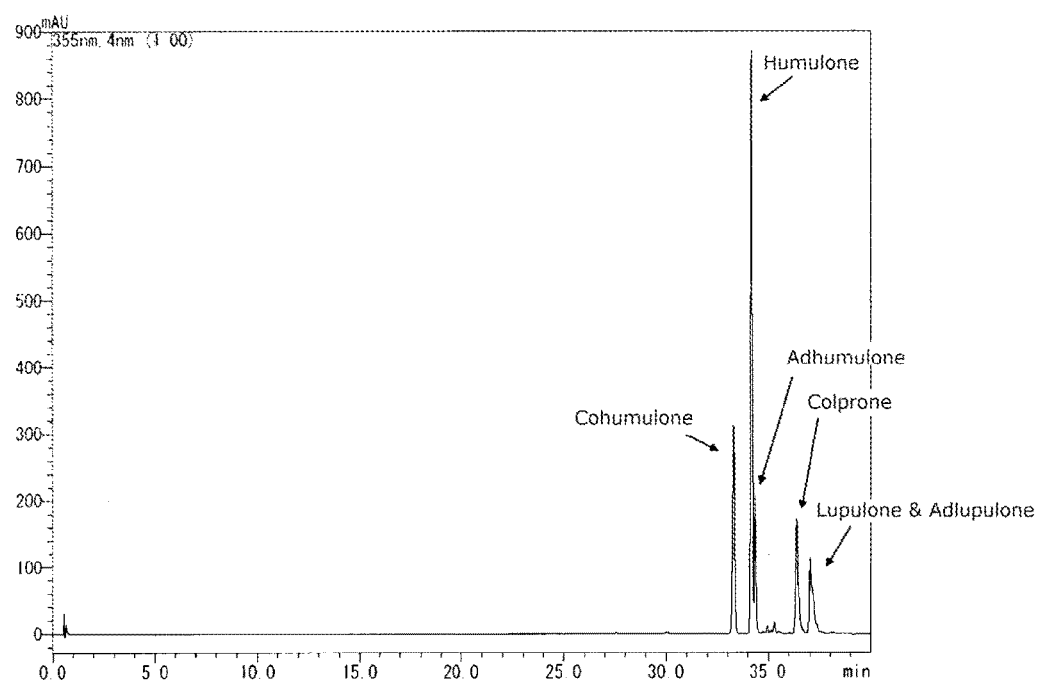
Figures 1, 4:
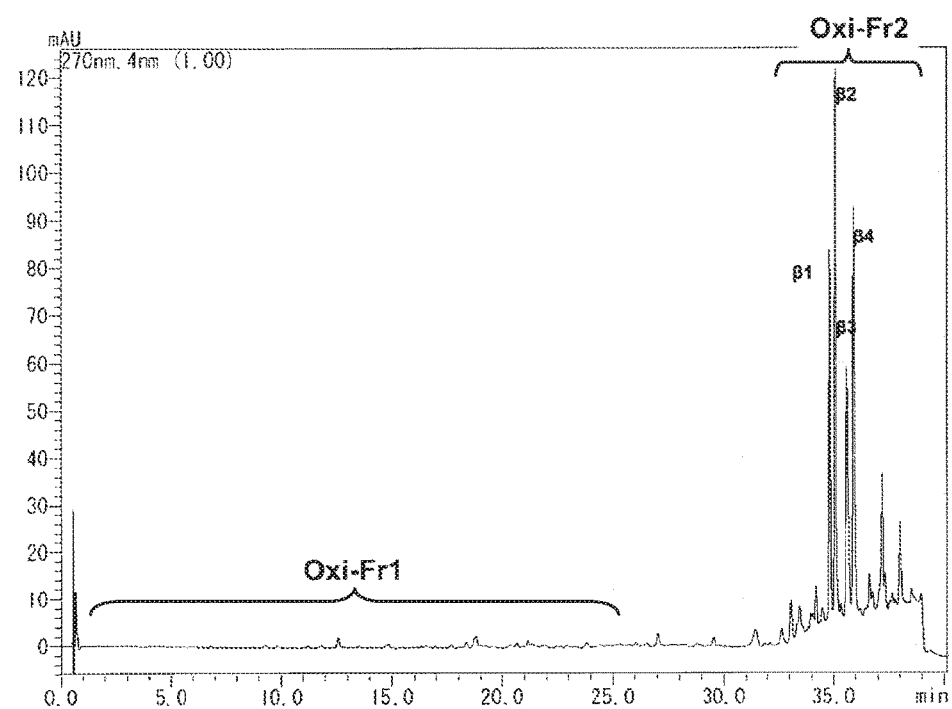
Figures 2, 4:
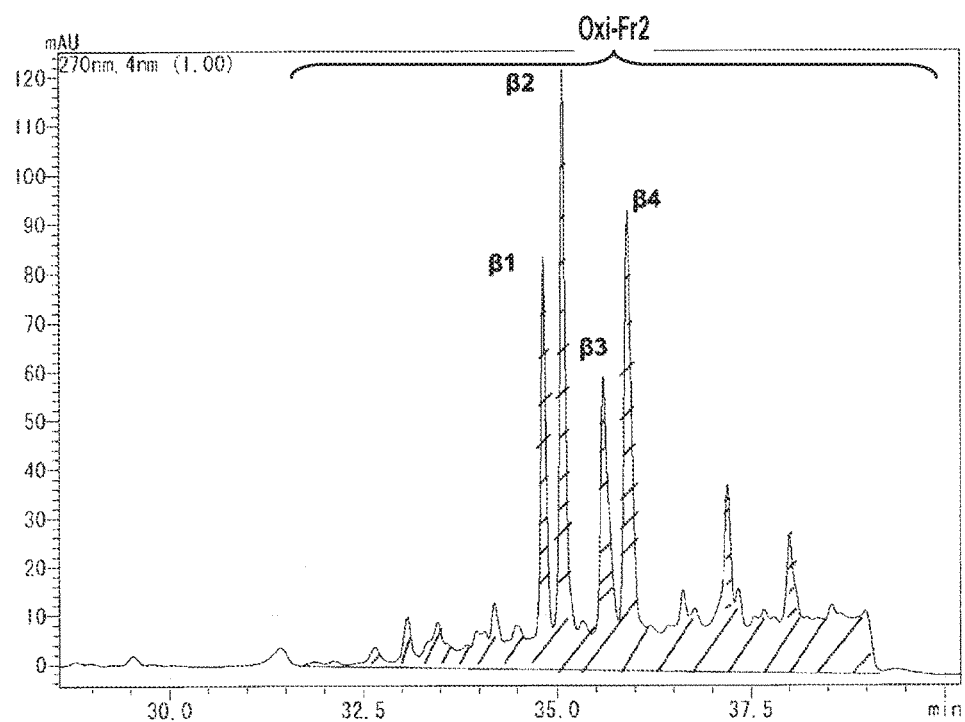
Figures 3, 4:
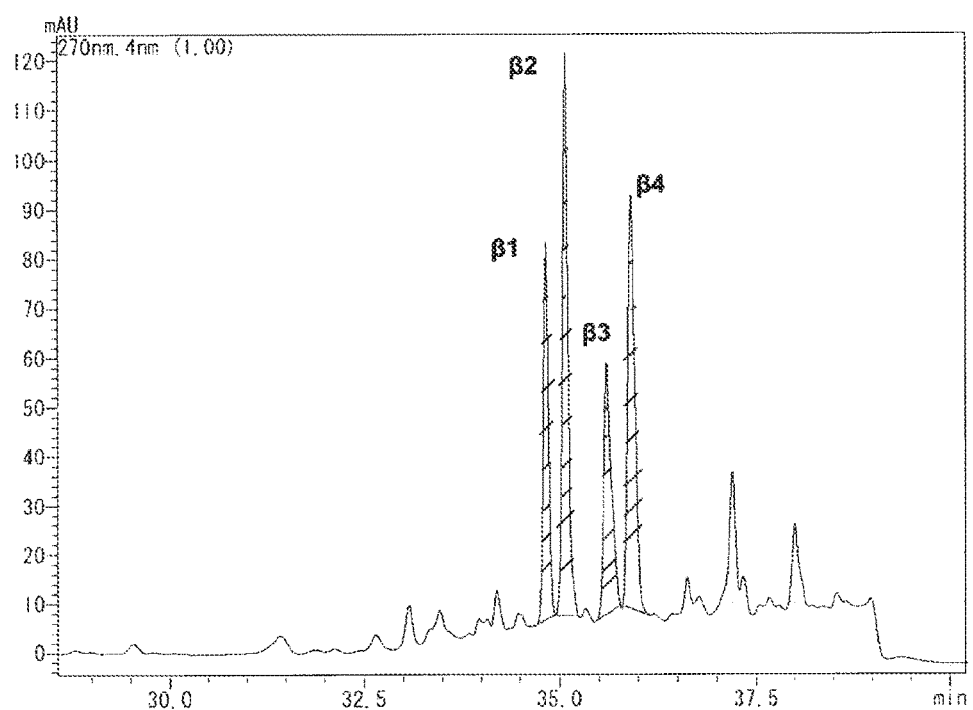
Figure 4:
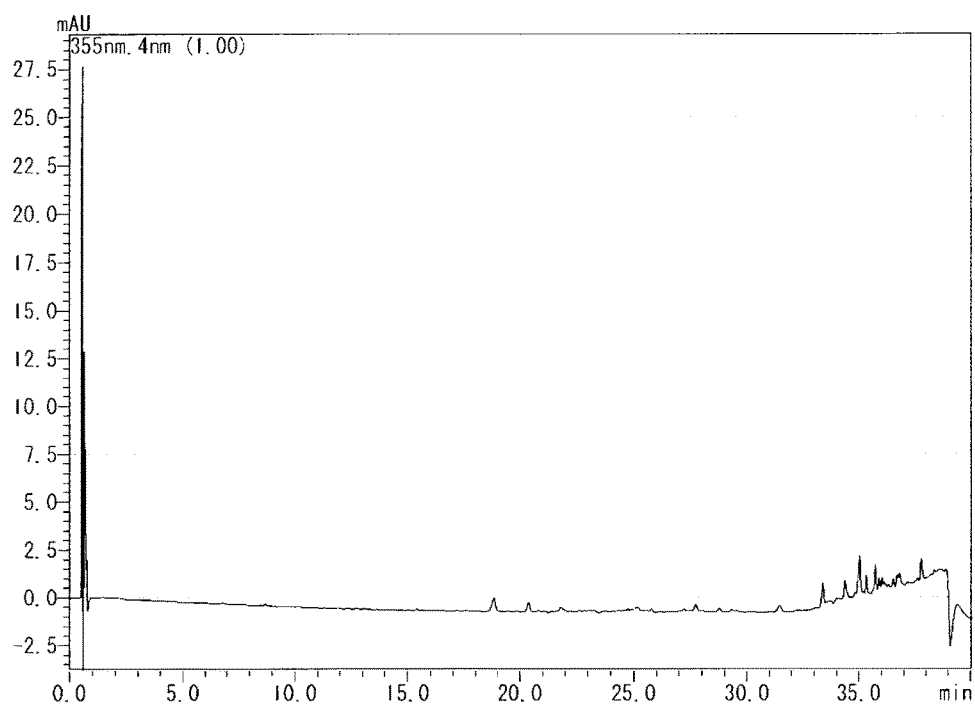

HPLC chromatograms obtained from the analysis of the hop extract oxidation-reaction product prepared in Example 1 are shown in FIGS. 2-1 to 2-3 (detection wavelength: 270 nm) and FIG. 2-4 (detection wavelength: 355 nm). Chromatograms from the analysis of the hop extract used as a raw material are also shown in FIGS. 3-1 and 3-2 (detection wavelength: 270 nm), and FIG. 3-3 (detection wavelength: 355 nm). A group of components designated as Oxi-Fr1 is detected in the region illustrated in FIG. 2-1. The summed value of the total peak area detected in the fraction is applied for the quantitative analysis. A group of components designated as Oxi-Fr2 is detected in the region illustrated in FIG. 2-2, FIG. 3-2. The area of the shaded portions is applied for the quantitative analysis. For each component of β1-4, the area of the shaded portions in the group of the peaks shown in FIG. 2-3 is applied for the quantitative analysis.

Figures 1, 5:
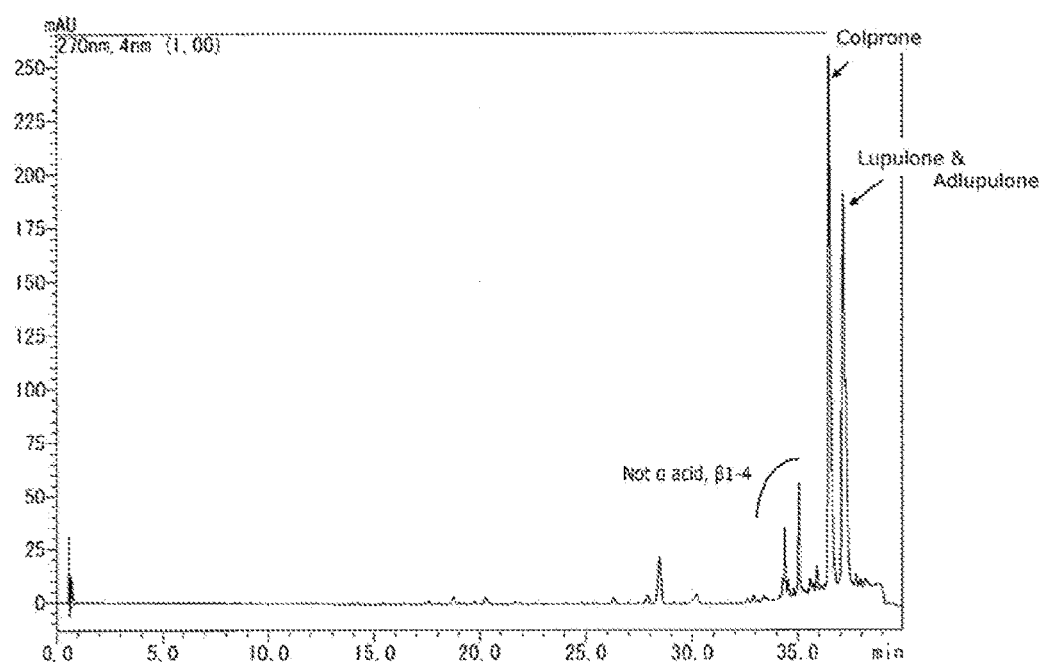
Figures 2, 5:
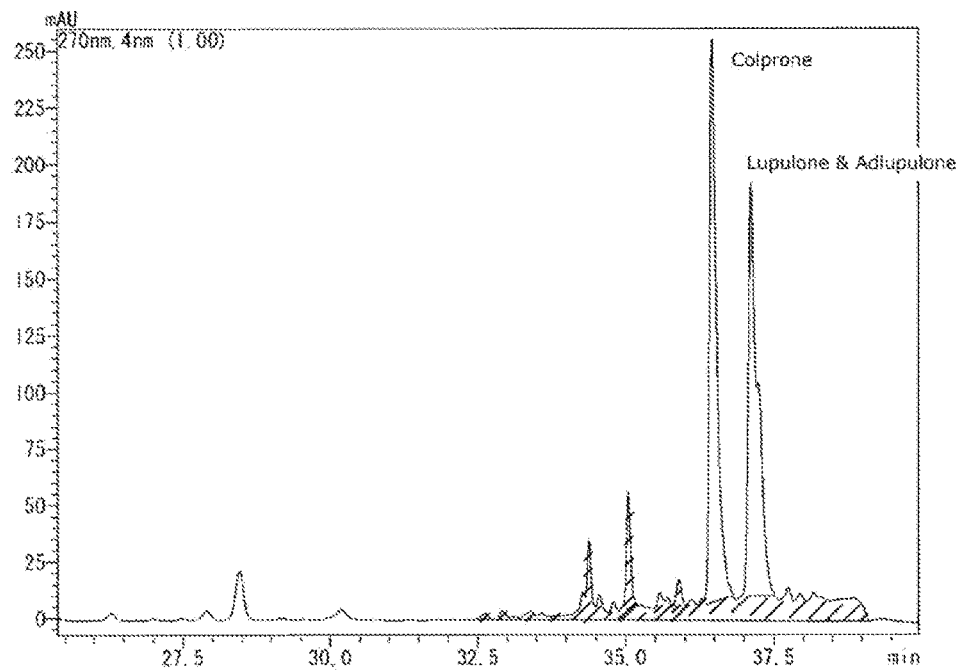
Figures 3, 5:
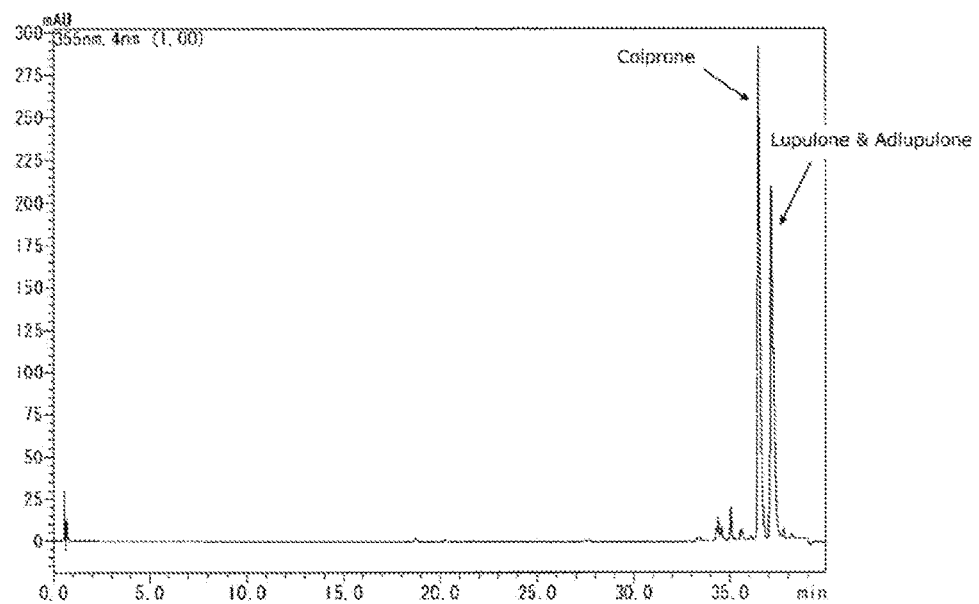

HPLC chromatograms obtained from the analysis of the hop extract oxidation-reaction product prepared in Example 2 are shown in FIGS. 4-1 to 4-3 (detection wavelength: 270 nm) and FIG. 4-4 (detection wavelength: 355 nm). Chromatograms from the analysis of the hop extract used as a raw material are also shown in FIGS. 5-1 and 5-2 (detection wavelength: 270 nm), and FIG. 5-3 (detection wavelength: 355 nm). A group of components designated as Oxi-Fr1 is detected in the region illustrated in FIG. 4-1 as in Example 1, but Oxi-Fr1 was only slightly produced because α acid and iso α acid are not contained in the raw extract used in Example 2. A group of components designated as Oxi-Fr2 is detected in the region illustrated in FIG. 4-2, FIG. 5-2 as in Example 1. The area of the shaded portions is used for the quantitative analysis. For each component of β1-4, the area of the shaded portions in the group of the peaks shown in FIG. 4-3 is applied for the quantitative analysis.

The results from Example 2 suggested that Oxi-Fr2 comprising each component of β1-4 is produced by oxidation of β acid in a hop extract.

A peak of each component of β1-4 produced by oxidation of β acid was fractionated to perform analysis in a mass spectrometer capable of precision mass measurement. The resulting measured values suggested that β1 and β2 are compounds in which one oxygen atom is added to colupulone, and β3 and β4 are compounds in which one oxygen atom added to lupulone, adlupulone.

Figures 1, 6:
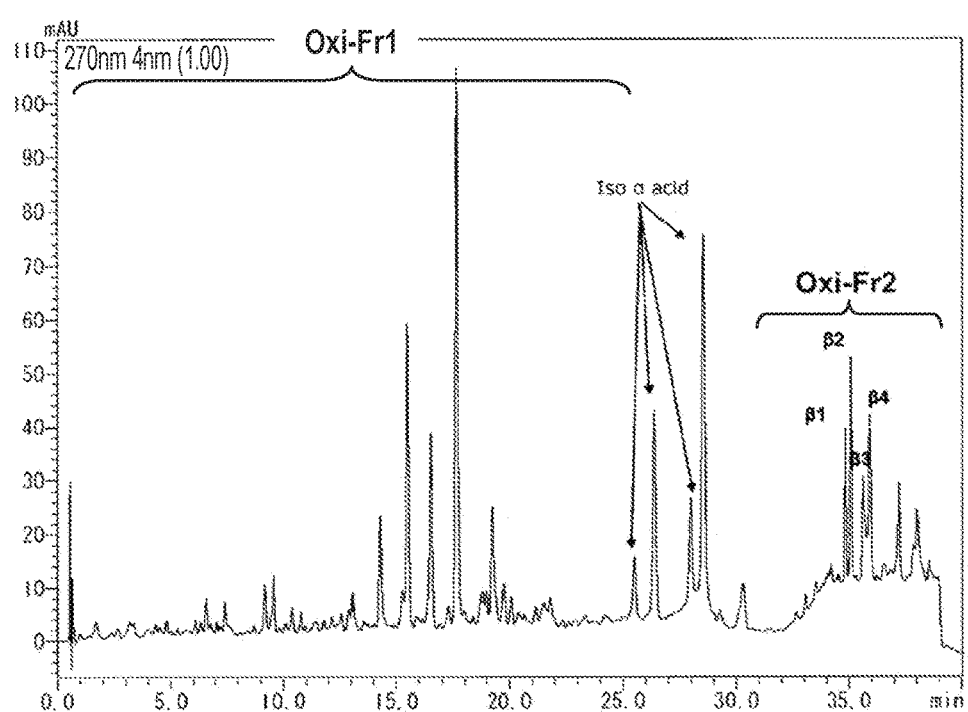
Figures 2, 6:
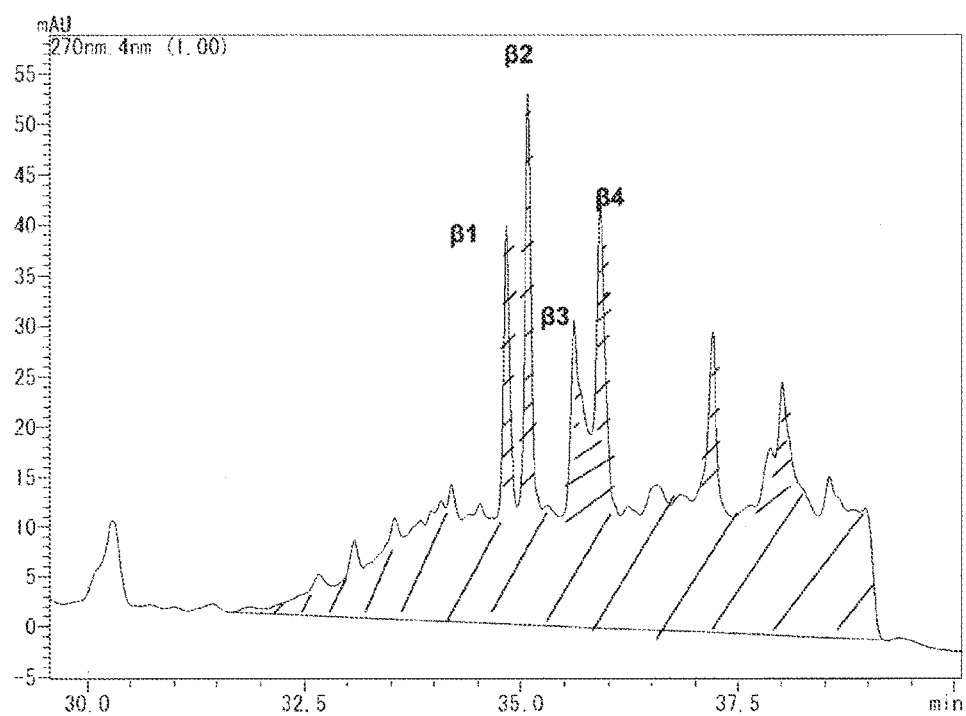
Figures 3, 6:
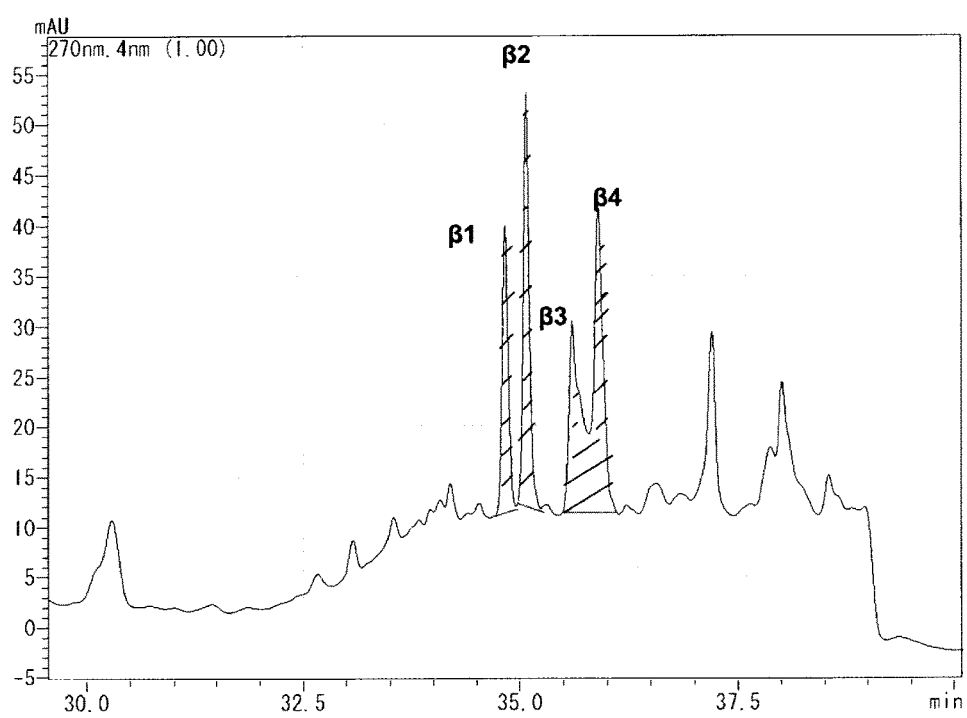
Figures 4, 6:
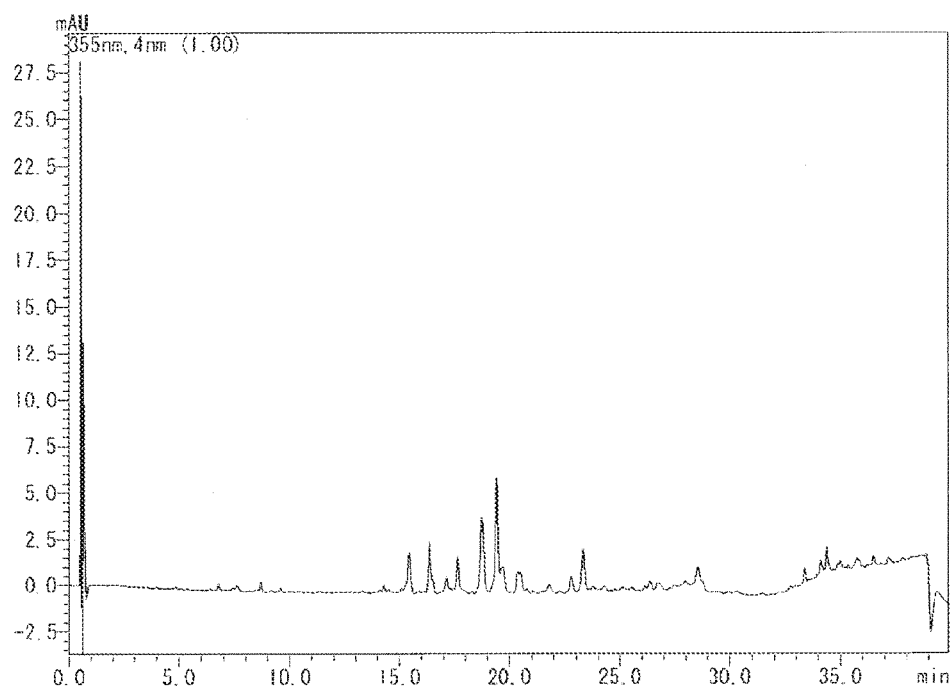
Figures 1, 7:
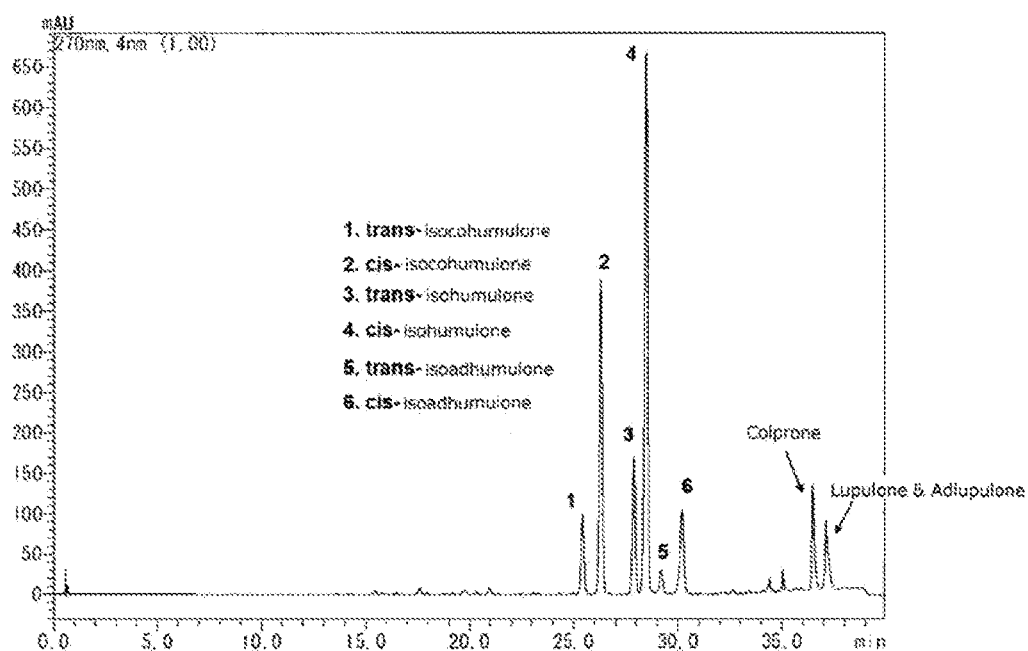
Figures 2, 7:
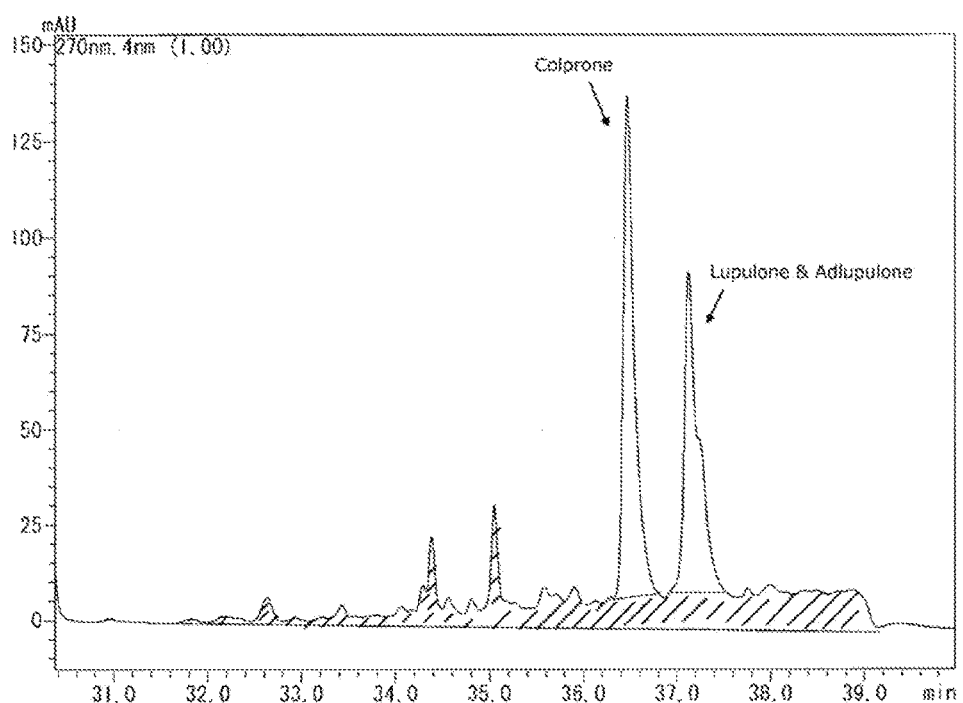
Figures 3, 7:
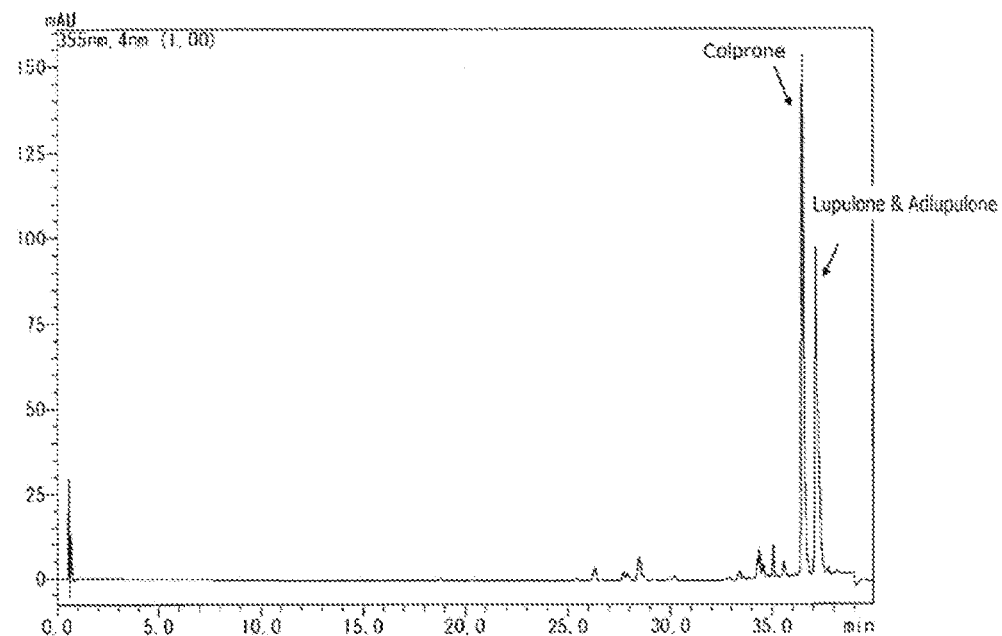

HPLC chromatograms from the analysis of the hop extract oxidation-reaction product prepared in Example 3 are shown in FIGS. 6-1 to 6-3 (detection wavelength: 270 nm) and FIG. 6-4 (detection wavelength: 355 nm). Chromatograms from the analysis of the hop extract used as a raw material are also shown in FIGS. 7-1 and 7-2 (detection wavelength: 270 nm) and FIG. 7-3 (detection wavelength: 355 nm). A group of components designated as Oxi-Fr1 is detected in the region illustrated in FIG. 6-1 as in Example 1. The summed value of the total peak area detected in the fraction is used for the quantitative analysis. A group of components designated as Oxi-Fr2 is also detected in the region illustrated in FIG. 6-2 and FIG. 7-2 as in Examples 1 and 2. The area of the shaded portions is used for the quantitative analysis. For each component of β1-4, the area of the shaded portions in the group of the peaks shown in FIG. 6-3 is used for the quantitative analysis.

Quantification Method

Oxi-Fr1, Oxi-Fr2 and β1-4 are quantified in terms of iso α acid equivalence based on each calculated value of area. Specifically, they can be quantified by using a standard curve produced with an iso α acid standard. α acid, β acid and iso α acid can be quantified by using a standard curve produced with a corresponding standard. For standards for α acid, β acid and iso α acid are, for example, Internal Calibration Standards: ICE-2, ICS-I2, ICS-T2 and the like available from American Society of Brewing Chemists (ASBC) can be used.

Calculation of Peak Area Ratios

By subjecting a hop extract to an oxidation-reaction, α acid, β acid and iso α acid in the extract decrease while the groups of components such as Oxi-Fr1 and Oxi-Fr2 increase. Therefore, a hop extract oxidation-reaction product can be evaluated by the ratio of peak area of α acid, β acid and iso α acid detected at a wavelength of 270 nm in the HPLC analysis to the total peak area of the components detected at the same wavelength. When calculating the total peak area, peaks detected in the region between the starting point of Oxi-Fr1 and the end point of Oxi-Fr2 are to be analyzed.

Weight ratios of "Oxi-Fr1/(α acid+iso α acid)," "β1-4/β acid" and "Oxi-Fr2/β acid" in each analyte sample were as shown in Table 1.

TABLE 2

|  | Oxi-Fr1/(α acid + iso α acid) | β1-4/β acid | Oxi-Fr2/β acid |
| --- | --- | --- | --- |
| Example 1 Raw extract | 0.00023 | 0.00056 | 0.39 |
| Example 1 Extract oxidation product | >30 | 36.0 | >100 |
| Example 2 Raw extract | — | 0.00031 | 0.25 |
| Example 2 Extract oxidation product | — | >50 | >100 |
| Example 3 Raw extract | 0.028 | 0.00064 | 0.46 |
| Example 3 Extract oxidation product | 2.8 | >50 | >100 |

(Since α acid and iso α acid are not contained in the raw extract used in Example 2, Oxi-Fr1/(α acid + iso α acid) can not be calculated.)

Clearly seen from the results of FIGS. 1, 2 and 3 and Table 2, α acid, β acid and iso α acid drastically decreased or disappeared in the hop extract oxidation-reaction product prepared by subjecting to an oxidation-reaction after powderization. The proportion of peak area of α acid, β acid and iso α acid to the total peak area of the hop extract oxidation-reaction product in the HPLC analysis was 10% or less in Examples 1 and 2, and 15.1% in Example 3.

Moreover, Oxi-Fr1, Oxi-Fr2 and β1-4 newly appeared or drastically increased in the hop extract prepared by subjecting to an oxidation-reaction after powderization.

Example 5

Sixty grams of the hop extract prepared by supercritical carbon dioxide extraction ($CO_2$ Hop Extract; α acid 55.6% w/w, β acid 22.6% w/w, iso α acid not detected; Hopsteiner) and 180 g of dextrin (TK-16; Matsutani Chemical Industry Co., Ltd.) were mixed to uniformity in a weight ratio of 1:3, and then the hop extract was powderized. The resulting powdered hop extract was heated at 40° C., 60° C., 80° C. for 8 hours to 196 hours for an oxidation-reaction. During the oxidation-reaction, samples were taken out over time and analyzed by the method described in Example 4 to determine weight ratios of "Oxi-Fr1/(α acid+iso α acid)," "β1-4/β acid" and "Oxi-Fr2/β acid" in each analyte sample. The results are shown in Table 3.

TABLE 3

| Heating temperature | Reaction time | Oxi-Fr1/(α acid + iso α acid) | β1-4/β acid | Oxi-Fr2/β acid |
| --- | --- | --- | --- | --- |
| 80° C. | 4 | >30 | 33 | >100 |
|  | 8 | >30 | 32 | >100 |
|  | 24 | >30 | 36 | >100 |
|  | 48 | >30 | 39 | >100 |
|  | 72 | >30 | 46 | >100 |
|  | 196 | >30 | 39 | >100 |
| 60° C. | 4 | 0.00026 | 0.016 | 0.34 |
|  | 8 | 0.00027 | 0.016 | 0.35 |
|  | 24 | 0.12 | 0.37 | 2.4 |
|  | 48 | >30 | 13 | >100 |
|  | 72 | >30 | 12 | >100 |
|  | 196 | >30 | 7.7 | 88 |
| 40° C. | 24 | 0.00023 | 0.014 | 0.32 |
|  | 48 | 0.00025 | 0.014 | 0.35 |
|  | 72 | 0.0041 | 0.014 | 0.35 |
|  | 196 | 0.011 | 0.017 | 0.36 |

Figures 1, 8:
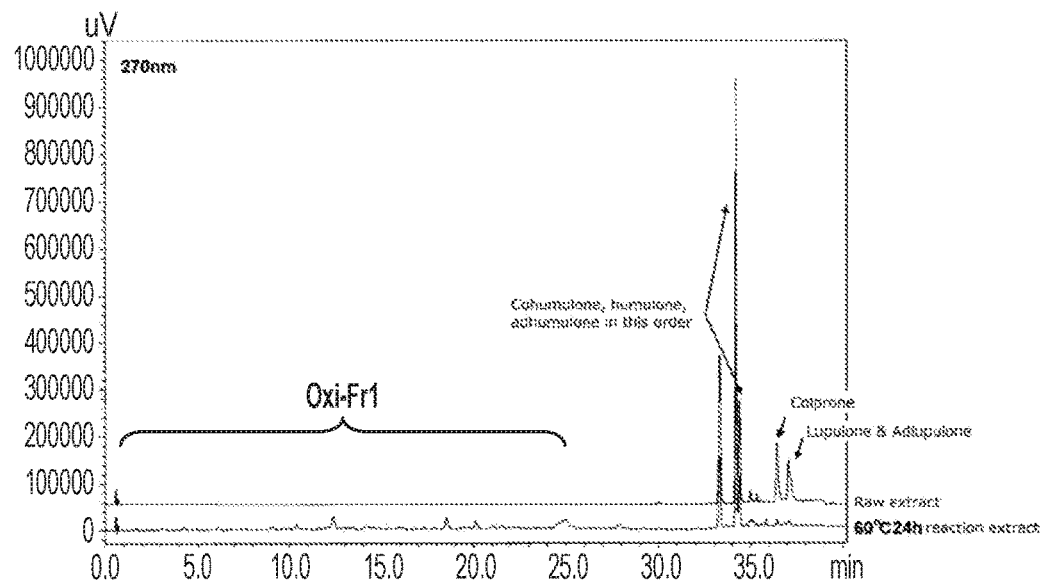
Figures 2, 8:
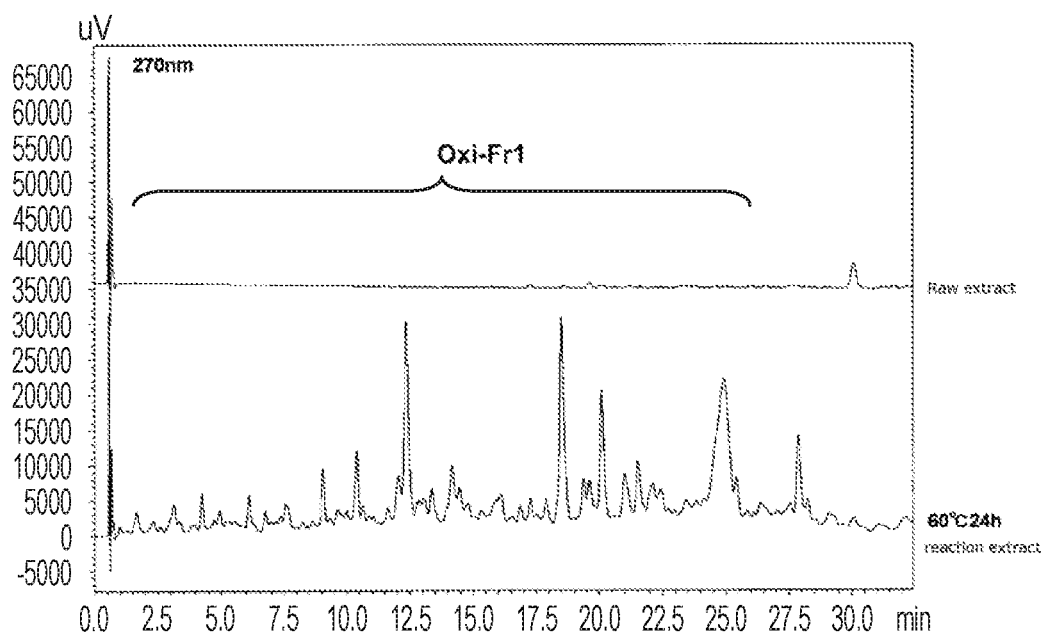
Figures 3, 8:
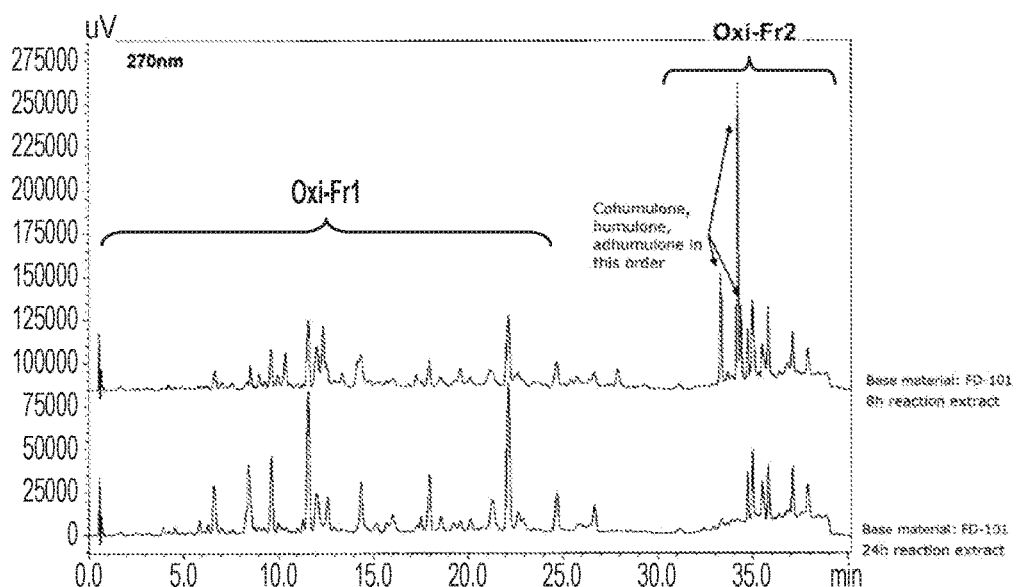
Figures 4, 8:
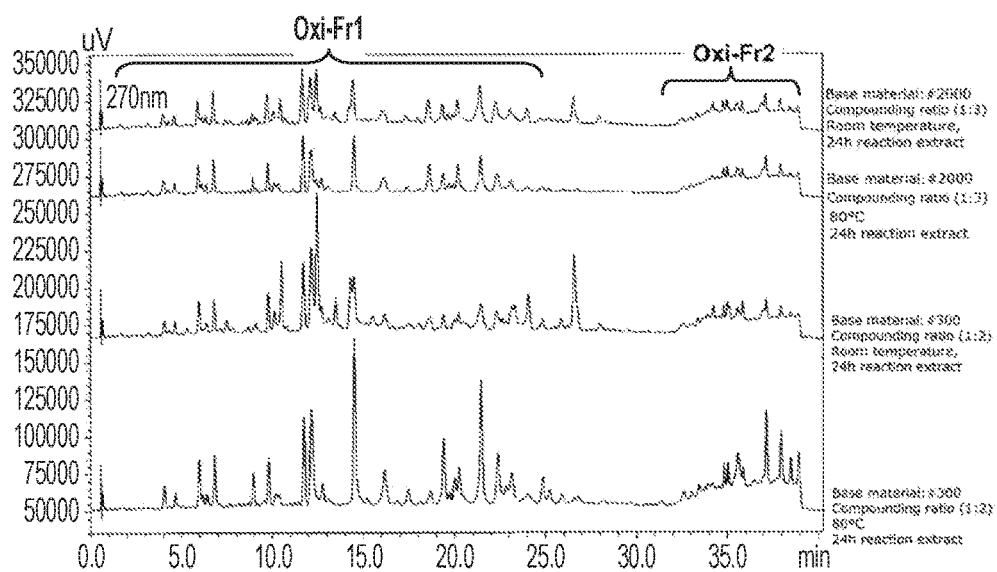
Figures 5, 8:
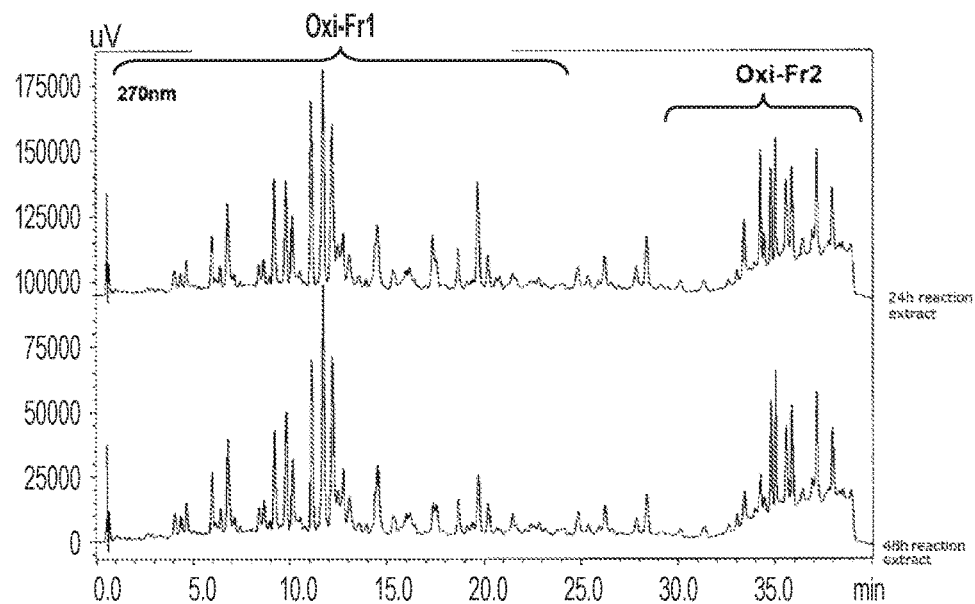
Figures 6, 8:
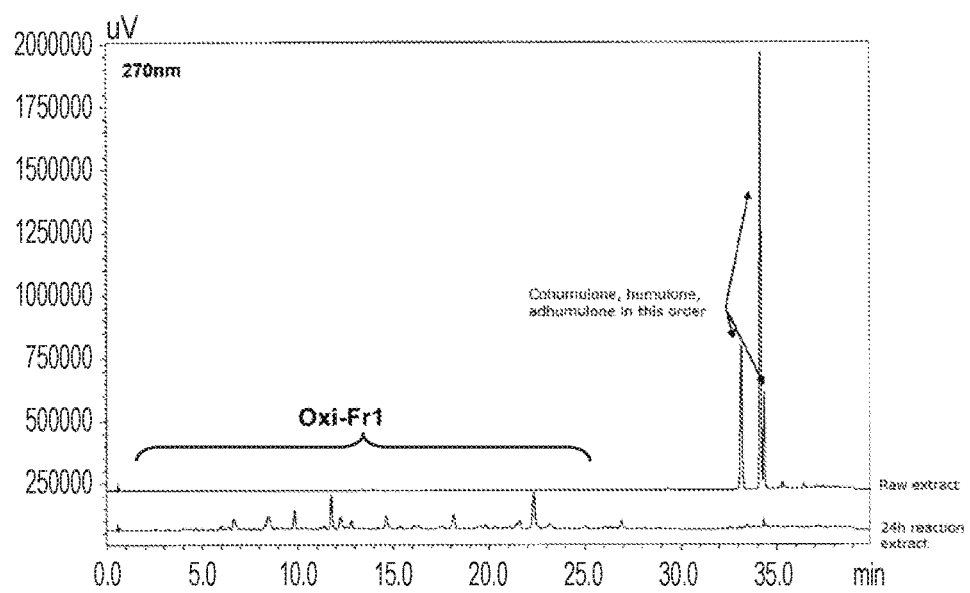
Figures 7, 8:
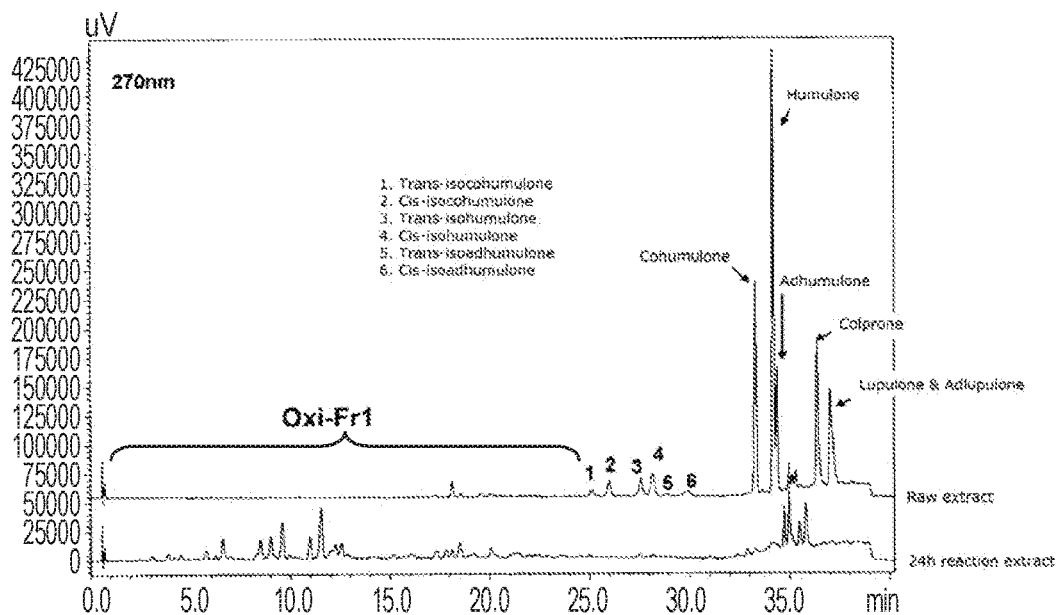
Figure 8:
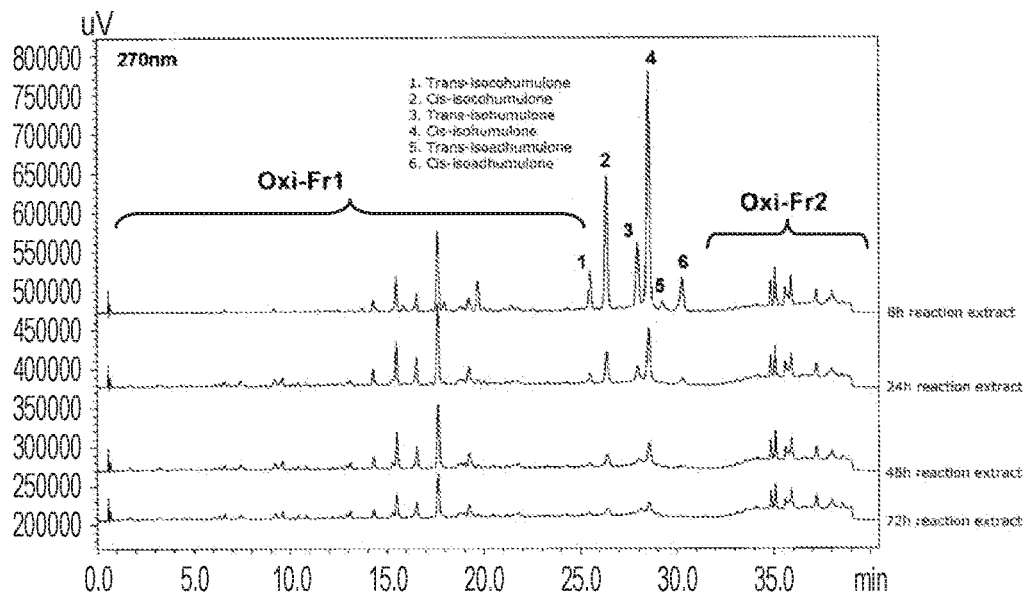

As clearly seen from Table 3, in a case where dextrin was used as a base material for powering, an oxidation-reaction was found to progress more rapidly when a reaction temperature of the oxidation-reaction was higher. FIG. 8-1 and FIG. 8-2 show component profiles of the raw extract and the extract oxidation-reaction products heated at 60° C. for 24 hours.

Example 6

Twenty grams of the hop extract prepared by supercritical carbon dioxide extraction ($CO_2$ Hop Extract; α acid 55.6% w/w, β acid 22.6% w/w, iso α acid not detected; Hopsteiner) and dextrin (TK-16; Matsutani Chemical Industry Co., Ltd.) were mixed to uniformity in a weight ratio of 1:2 to 1:9, and then the hop extract was powderized. The resulting powdered hop extract was heated at 80° C. for 8 hours to 48 hours for an oxidation-reaction. During the oxidation-reaction, samples were taken out over time and analyzed by the method described in Example 4 to determine weight ratios of "Oxi-Fr1/(α acid+iso α acid)," "β1-4/β acid" and "Oxi-Fr2/β acid" in each analyte sample. The results are shown in Table 4.

TABLE 4

| Raw extract:Dextrin | Reaction time | Oxi-Fr1/(α acid + iso α acid) | β1-4/β acid | Oxi-Fr2/β acid |
| --- | --- | --- | --- | --- |
| 1:9 | 8 | 3.5 | 15 | 61 |
|  | 24 | >30 | 27 | >100 |
|  | 48 | >30 | 8.3 | 65 |
| 1:5 | 8 | 6.8 | 22 | 90 |
|  | 24 | >30 | 49 | >100 |
|  | 48 | >30 | 37 | >100 |
| 1:3 | 8 | 1.1 | 10 | 39 |
|  | 24 | >30 | >50 | >100 |
|  | 48 | >30 | 47 | >100 |
| 1:2 | 8 | 0.17 | 0.48 | 1.9 |
|  | 24 | 1.3 | 1.4 | 5.9 |
|  | 48 | 8.6 | 15 | >100 |
| 1:1 | 8 | 0.034 | 0.13 | 0.64 |
|  | 24 | 0.044 | 0.20 | 0.76 |
|  | 48 | 0.077 | 0.24 | 1.2 |

In a case where the raw extract and dextrin were in a ratio of 1:1, the extract formed lumps without forming uniform powder, and the reaction efficiency decreased. In contrast, it formed completely uniform powder in the case of 1:3 to 1:9, and the reaction progressed efficiently. When the ratio of the extract and dextrin changed, the component profiles of the extract oxidation-reaction products themselves did not change.

Example 7

Twenty grams of the hop extract prepared by supercritical carbon dioxide extraction ($CO_2$ Hop Extract; α acid 55.6% w/w, β acid 22.6% w/w, iso α acid not detected; Hopsteiner) and carbohydrate-based excipients (dextrin: TK-16, Max1000; both from Matsutani Chemical Industry Co., Ltd.; cellulose: FD101, ST100; both from Asahi Kasei Chemicals Corporation) were mixed to uniformity in a weight ratio of 1:3, and then the hop extract was powderized. The resulting powdered hop extract was heated at 80° C. for 8 hours to 93 hours for an oxidation-reaction. During the oxidation-reaction, samples were taken out over time and analyzed by the method described in Example 4 to determine weight ratios of "Oxi-Fr1/(α acid+iso α acid)," "β1-4/β acid" and "Oxi-Fr2/β acid" in each analyte sample. The results are shown in Table 5.

TABLE 5

| Base material for powdering (lipid based) | Reaction time | Oxi-Fr1/(α acid + iso α acid) | β1-4/β acid | Oxi-Fr2/β acid |
|---|---|---|---|---|
| Dextrin (TK-16) | 8 | 1.1 | 10 | 39 |
| | 24 | >30 | >50 | >100 |
| | 48 | >30 | 47 | >100 |
| Dextrin (Max 1000) | 8 | 0.76 | 8.1 | 45 |
| | 24 | >30 | 46 | >100 |
| | 48 | >30 | 38 | >100 |
| Cellulose (ST-100) | 8 | 0.67 | 1.6 | 6.0 |
| | 24 | >30 | >50 | >100 |
| | 48 | >30 | 43 | >100 |
| | 93 | >30 | 44 | >100 |
| Cellulose (FD-101) | 8 | 0.64 | 1.1 | 6.1 |
| | 24 | >30 | >50 | >100 |
| | 48 | >30 | >50 | >100 |
| | 93 | >30 | 12 | 67 |

When any base materials were used, the oxidation-reaction progressed in a similar way. The component profiles of the oxidation-reaction products were also similar. The proportion of the peak area of iso α acid, α acid and β acid to the total peak area of the hop extract oxidation-reaction product after a reaction time of 8 hour was 15% or less as determined by HPLC analysis while the proportion of the peak area of iso α acid, α acid and β acid to the total peak area of the hop extract oxidation-reaction product after a reaction time of 24 hour or longer was 10% or less as determined by HPLC analysis. Further, FIG. 8-3 shows the component profile of the extract oxidation-reaction product after heating the extract which was powderized using FD-101, at 80° C. for 8 hours, 24 hour.

Example 8

Twenty grams of the hop extract prepared by supercritical carbon dioxide extraction ($CO_2$ Hop Extract; α acid 55.6% w/w, β acid 22.6% w/w, iso α acid not detected; Hopsteiner) and diatomaceous earth (Rajioraito #2000, #300; Showa Chemical Industry Co., Ltd.) were mixed to uniformity in a weight ratio of 1:2 to 1:3, and then the hop extract was powderized. The resulting powdered hop extract was heated at 80° C. for 4 hours to 48 hours for an oxidation-reaction. During the oxidation-reaction, samples were taken out over time and analyzed by the method described in Example 4 to determine weight ratios of "Oxi-Fr1/(α acid+iso α acid)," "β1-4/β acid" and "Oxi-Fr2/β acid" in each analyte sample. The results are shown in Table 6.

TABLE 6

| Base material for powdering (compounding ratio), reaction temperature | Reaction time | Oxi-Fr1/(α acid + iso α acid) | β1-4/β acid | Oxi-Fr2/β acid |
|---|---|---|---|---|
| #2000(1:3) Room temperature | 4 | 16 | 6.5 | 59 |
| | 24 | 25 | 9.0 | >100 |
| | 48 | >30 | 1.8 | 56 |
| #2000(1:3) 80° C. | 4 | >30 | 11 | >100 |
| | 24 | >30 | 13 | >100 |
| | 48 | >30 | 12 | >100 |
| #2000(1:2) 80° C. | 4 | >30 | 16 | >100 |
| | 24 | >30 | 23 | >100 |
| | 48 | >30 | 45 | >100 |
| #300(1:2) Room temperature | 4 | 2.7 | 1.3 | 13 |
| | 24 | 25 | 9.0 | >100 |
| | 48 | >30 | 2.0 | 59 |
| #300(1:2) 80° C. | 4 | 6.4 | 4.8 | 55 |
| | 24 | >30 | 3.7 | 62 |
| | 48 | >30 | 4.0 | 67 |

In a case where diatomaceous earth was used for a base material for powdering, the reaction efficiently progressed without heating upon the oxidation-reaction. The proportion of the peak area of iso α acid, α acid and β acid to the total peak area of the hop extract oxidation-reaction product as determined by HPLC analysis was 10% or less. The reaction efficiently progressed without heating because metals contained in diatomaceous earth appeared to serve as a catalyst of the oxidation-reaction. The result suggests that the reaction efficiency can be increased by using a metal-containing base material. FIG. 8-4 shows profiles of the extract oxidation-reaction products prepared by the reaction under each condition.

Example 9

Twenty grams of the hop extract prepared by supercritical carbon dioxide extraction ($CO_2$ Hop Extract; α acid 55.6% w/w, β acid 22.6% w/w, iso α acid not detected; Hopsteiner) and ground hop lees (BP55; Hopsteiner) were mixed to uniformity in a weight ratio of 1:3, and then the hop extract was powderized. The resulting powdered hop extract was heated at 80° C. for 24 hours to 48 hours for an oxidation-reaction. During the oxidation-reaction, samples were taken out over time and analyzed by the method described in Example 4 to determine weight ratios of "Oxi-Fr1/(α acid+ iso α acid)," "β1-4/β acid" and "Oxi-Fr2/β acid" in each analyte sample The results are shown in Table 7.

TABLE 7

| | Reaction time | Oxi-Fr1/(α acid + iso α acid) | β1-4/β acid | Oxi-Fr2/β acid |
|---|---|---|---|---|
| Hop-lees (BP-55 is used)-is used as a base material for powdering | 24 | 13 | >50 | >100 |
| | 48 | 20 | >50 | >100 |

When hop lees were used as a base material for powdering, the oxidation-reaction efficiently progressed. Each of the proportion of the peak area of iso α acid, α acid and β acid to the total peak area of the hop extract oxidation-reaction product as determined by HPLC analysis was 10% or less. FIG. 8-5 shows profiles of the extract oxidation-reaction products.

Example 10

Ten grams of the hop extract (α acid 94.4% w/w, β acid 3.36% w/w, iso α acid not detected) prepared by fractionating an α acid fraction from the hop extract prepared by supercritical carbon dioxide extraction ($CO_2$ Hop Extract; Hopsteiner) and dextrin (TK-16; Matsutani Chemical Industry Co., Ltd.) were mixed to uniformity in a weight ratio of 1:3, and then the hop extract was powderized. The resulting powdered hop extract was heated at 80° C. for 8 hours to 72 hours for an oxidation-reaction. During the oxidation-reaction, samples were taken out over time and analyzed by the method described in Example 4 to determine weight ratios of "Oxi-Fr1/(α acid+iso α acid)," "β1-4/β acid" and "Oxi-Fr2/β acid" in each analyte sample. The results are shown in Table 8.

TABLE 8

| Reaction time | Oxi-Fr1/(α acid + iso α acid) | β1-4/ β acid | Oxi-Fr2/ β acid |
| --- | --- | --- | --- |
| 0 | 0.00013 | — | — |
| 8 | 0.020 | — | — |
| 24 | 26 | — | — |
| 48 | 23 | — | — |
| 72 | 29 | — | — |

Since the amount of β acid relative to the amount of α acid in the raw extract is very low, parameters for β acid are not taken into account. It was found that oxidation of α acid produced mainly Oxi-Fr1. Each of the proportion of the peak area of iso α acid, α acid and β acid to the total peak area of the hop extract oxidation-reaction product after a reaction time of 24 hour or longer was 10% or less. FIG. 8-6 shows component profiles of the extract used as a raw material and the extract oxidation-reaction product which was subjected to an oxidation-reaction for 24 hours.

Example 11

Twenty grams of the hop extract prepared by ethanol extraction (EtOH Hop Extract; α acid 31.8% w/w, β acid 24.8% w/w, iso α acid 2.77%; Hopsteiner) and cellulose (FD-101; Asahi Kasei Chemicals Corporation) were mixed to uniformity in a weight ratio of 1:3, and then the hop extract was powderized. The resulting powdered hop extract was heated at 80° C. for 8 hours to 24 hours for an oxidation-reaction. During the oxidation-reaction, samples were taken out over time and analyzed by the method described in Example 4 to determine weight ratios of "Oxi-Fr1/(α acid+iso α acid)," "β1-4/β acid" and "Oxi-Fr2/β acid" in each analyte sample. The results are shown in Table 9.

TABLE 9

| Reaction time | Oxi-Fr1/(α acid + iso α acid) | β1-4/ β acid | Oxi-Fr2/ β acid |
| --- | --- | --- | --- |
| 8 | 14 | >50 | >100 |
| 24 | 12 | >50 | >100 |

When the hop extract prepared by ethanol extraction was used as a raw material, the oxidation-reaction was found to progress. Each of the proportion of the peak area of iso α acid, α acid and β acid to the total peak area of the hop extract oxidation-reaction product as determined by HPLC was 10% or less. FIG. 8-7 shows component profiles of the extract used as a raw material and the extract oxidation-reaction product which was subjected to an oxidation-reaction for 24 hours.

Example 12

Twenty grams of the hop extract isomerized after extracted by supercritical carbon dioxide extraction (Isomerized Kettle Extract: iso α acid 53.0% w/w, β acid 20.0% w/w, α acid not detected; Hopsteiner) and dextrin (TK-16; Matsutani Chemical Industry Co., Ltd.) were mixed to uniformity in a weight ratio of 1:3, and then the hop extract was powderized. The resulting powdered hop extract was heated at 80° C. for 8 hours to 72 hours for an oxidation-reaction. During the oxidation-reaction, samples were taken out over time and analyzed by the method described in Example 4 to determine weight ratios of "Oxi-Fr1/(α acid+ iso α acid)," "β1-4/β acid" and "Oxi-Fr2/β acid" in each analyte sample. The results are shown in Table 10.

TABLE 10

| Reaction time | Oxi-Fr1/(α acid + iso α acid) | β1-4/ β acid | Oxi-Fr2/ β |
| --- | --- | --- | --- |
| 8 | 0.25 | >50 | >100 |
| 24 | 2.8 | >50 | >100 |
| 48 | 6.7 | >50 | >100 |
| 72 | 7.0 | >50 | >100 |

When the extract isomerized to enrich iso α acid was used as a raw material, the oxidation-reaction was found to progress. The proportion of the peak area of iso α acid, α acid and β acid to the total peak area of the hop extract oxidation-reaction product as determined by HPLC was 44.9% when a reaction time was 8 hours, 15.1% when a reaction time was 24 hours, and 10% or less when a reaction time was 48 hours or longer. FIG. 8-3 shows component profiles of the extract oxidation-reaction products subjected to an oxidation-reaction for 8 hours to 72 hours.

Example 13

Sensory Evaluation

The hop extract oxidation-reaction products obtained in Examples 1, 2, 3, 5, 7 to 12 were compared with the hop extract for bitter and harsh tastes by sensory evaluation.

Evaluation Method in the Sensory Evaluation of Bitter and Harsh Tastes

The hop extract oxidation-reaction products obtained in Examples 1, 2, 3, 5 to 12 and, as Comparative Examples, a hop extract used as a raw material for the hop extract oxidation-reaction products and an isomerized hop extract (IsoExtract 30%; Hopsteiner) were tested for bitter and harsh tastes by sensory evaluation by 8 in-house staffs as described below. For the hop extract oxidation-reaction products obtained in Examples 1, 2, 5, 7 to 12, each was added to 10 mM citrate buffer (pH 5.5) to give a sample so that the sample contained an equivalent amount of oxidation-reaction products that would be generated from the total 50 ppm of α acid, iso α acid and β acid in the raw material. For the Comparative Examples, each was added to 10 mM citrate buffer (pH 5.5) to give a sample so that the total amount of α acid, iso α acid and β acid was 50 ppm.

In the sensory evaluation, several mL of a sample was put into the mouth, and evaluated according to the evaluation criteria. The result was calculated as the mean of the scores from the 8 staffs.

Evaluation Criteria

TABLE 11

| Evaluation items | Valuation criteria | Score |
|---|---|---|
| Bitter and harsh tastes | Bitter and harsh tastes are not sensed. | 0 point |
| | Bitter and harsh tastes are slightly sensed. | 1 point |
| | Bitter and harsh tastes are sensed. | 2 point |
| | Bitter and harsh tastes are strongly sensed. | 3 point |
| | Bitter and harsh tastes are sensed too strongly to drink. | 4 point |

Evaluation Results

TABLE 12

| Extract used:base material (compounding ratio) Heating temperature, time | Oxi-Fr1/(α acid + iso α acid) | β1-4/β acid | Oxi-Fr2/β acid | The ratio of the peak area of α acid, iso α acid and β acid to the total peak area (%) | Example | Compartive Example | Score for bitter and harsh tastes |
|---|---|---|---|---|---|---|---|
| CO2 extract | 0.000 | 0.001 | 0.39 | 82.6 | | ○ | 2.86 |
| β aroma extract | — | 0.000 | 0.25 | 55.8 | | ○ | 2.57 |
| EtOH extract | 0.042 | 0.001 | 0.45 | 65.5 | | ○ | 3.13 |
| Isomerized hop extract | 0.000 | — | — | 88.4 | | ○ | 4.00 |
| CO2 extract:TK-16 (1:3) 60° C. 24 h | 0.12 | 0.37 | 2.4 | 28.2 | 5 | | 1.71 |
| CO2 extract:FD-101 (1:3) 80° C. 8 h | 0.64 | 1.1 | 6.1 | 11.5 | 7 | | 1.43 |
| CO2 extract:TK-16 (1:3) 80° C. 24 h | >30 | 36 | >100 | <10 | 1 | | 0.714 |
| CO2 extract:#2000 (1:3) room temperature 24 h | 25 | 9.0 | >100 | <10 | 8 | | 0.500 |
| CO2 extract:#2000 (1:3) 80° C. 24 h | >30 | 13 | >100 | <10 | 8 | | 0.750 |
| CO2 extract:#300 (1:2) room temperature 24 h | 25 | 9.0 | >100 | <10 | 8 | | 0.750 |
| CO2 extract:#300 (1:2) 80° C. 24 h | >30 | 3.7 | 62 | <10 | 8 | | 0.875 |
| CO2 extract:BP55 (1:3) 80° C. 48 h | 20 | >50 | >100 | <10 | 9 | | 0.875 |
| α acid extract:TK-16 (1:3) 80° C. 24 h | 26 | 23 | >100 | <10 | 10 | | 0.625 |
| β aroma extract:TK-16 (1:3) 80° C. 24 h | — | >50 | >100 | <10 | 2 | | 1.43 |
| IKE extract:TK-16 (1:3) 80° C. 8 h | 0.25 | >50 | >100 | 44.9 | 12 | | 2.00 |
| IKE extract:TK-16 (1:3) 80° C. 24 h | 2.8 | >50 | >100 | 15.1 | 3 | | 2.14 |
| IKE extract:TK-16 (1:3) 80° C. 48 h | 6.7 | >50 | >100 | <10 | 12 | | 1.38 |
| EtOH extract:FD-101 (1:3) 80° C. 24 h | 12 | >100 | >100 | <10 | 11 | | 1.63 |

The results suggested that the hop extract oxidation-reaction products obtained in Examples 1, 2, 3, 5, 7 to 12 had drastically reduced bitter and harsh tastes and a flavor suitable for a drink. Specifically, the results showed that a hop extract oxidation-reaction product having "Oxi-Fr1/(α acid+iso α acid)" of 0.1 or more by weight ratio, "(β1+β2+β3+β4)/β acid" of 0.3 or more by weight ratio and "Oxi-Fr2/β acid" of 2.0 or more by weight ratio (Examples) had reduced bitter and harsh tastes as compared with other hop extracts (Comparative Examples). Further, when evaluated by the peak area ratio, the results showed that a hop extract oxidation-reaction product in which the proportion of the peak area of α acid, iso α acid and β acid to the total peak area as determined by HPLC was 50% or less (Examples) had reduced bitter and harsh tastes as compared with other hop extracts.

Example 14

Evaluation of a Lipid Absorption Suppressing Effect of the Hop Extract Oxidation-Reaction Products A lipid absorption suppressing effect of the hop extract oxidation-reaction product obtained in Example 1 was evaluated by a single dose test of a lipid emulsion with a rat A test to measure the lipid emulsion absorption in a rat was performed as described below according to the reported method (Int. J. Obes. Relat. Metab. Disord. 25, 1459-1464 (2001). That is, a lipid emulsion was prepared by mixing and sonicating corn oil (6 ml), cholic acid (80 mg), cholesteryl oleate (2 g) and distilled water (2 ml), and orally administered to a 8 week old male Wistar rat (Charles River Laboratories Japan Inc.) via a stomach tube in a dose of 10 ml/kg weight after 16 hour fasting. For the group in which the hop extract oxidation-reaction product obtained in Example 1 was administered, the hop extract oxidation-reaction product was mixed when preparing a lipid emulsion so that the dose is 1000 mg/kg weight. Blood was each withdrawn from the caudal vein before the administration of the lipid emulsion, and 1, 2, 3, 4, 5 hours after the administration. Plasma was prepared in accordance with the standard method to measure a concentration of neutral fat in plasma by Triglyceride E Test Wako (Wako Pure Chemical Industries, Ltd.).

Figure 9:
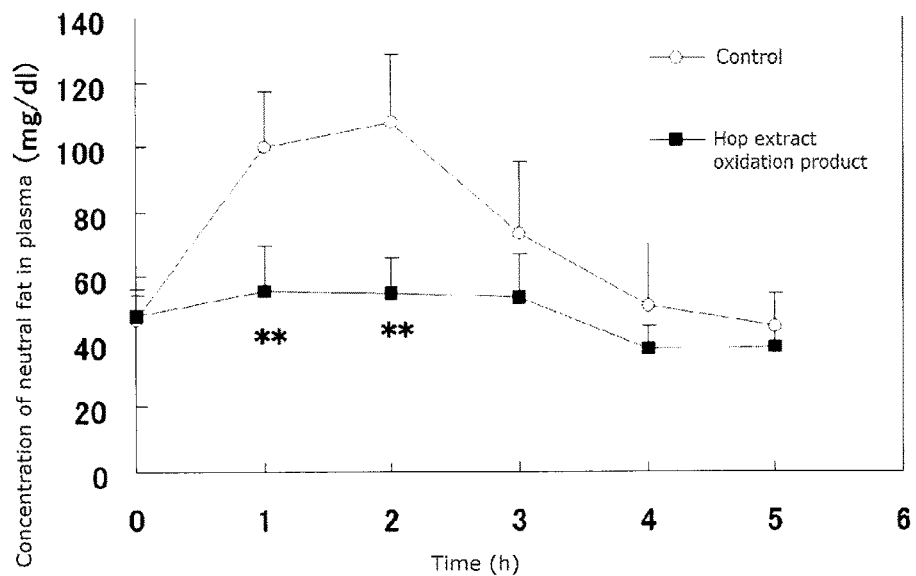
FIG. 9 shows a lipid absorption suppressing effect of a hop extract oxidation-reaction product.

The results showed that the concentration of neutral fat in plasma was increased 1 to 3 hours after the administration for the control group while the increase in the concentration of neutral fat in plasma was significantly suppressed 1 to 2 hours after administration for the group in which the hop extract oxidation-reaction product was administration (FIG. 9: a lipid absorption inhibitory effect of the hop extract oxidation-reaction product; the hop extract oxidation-reaction product was administered in a dose of 1000 mg/kg weight concurrently with the lipid emulsion. *: P<0.05, **: P<0.01 (as compared with the control group); the concentrations of neutral fat in blood before and after the administration were expressed as mean±standard deviation.). The above results indicated that the hop extract oxidation-reaction product has a lipid absorption suppressing effect. Neutral fat is decomposed by pancreatic lipase in the small intestine to be absorbed. Accordingly, a pancreatic lipase activity inhibitory effect of the hop extract oxidation-reaction product was evaluated since the pancreatic lipase activity significantly contributes to neutral fat absorption.

Example 15

Evaluation of a Pancreatic Lipase Activity Inhibitory Effect of the Hop Extract Oxidation-Reaction Product A pancreatic lipase activity inhibitory effect of the hop extract oxidation-reaction product obtained in Example 1 was evaluated. Measurements of pancreatic lipase activities were performed in accordance with the reported method as follows (J. Agric. Food Chem., 53, 4593-4598 (2005)). For a measurement reagent, 4-methylumbelliferyloleate (Sigma Aldrich) was used, and 10 U of swine pancreatic lipase (Sigma Aldrich) per one sample was used as an enzyme source. The hop extract oxidation-reaction products obtained in Examples 1, 2, 3, 5, 7 to 12 were dissolved to a predetermined concentration of a solid content (a concentration of oxidized ingredients originated from the hop extract) using 4% dimethyl sulfoxide, and subjected to a test. Activities were expressed as the enzyme activity obtained when only 4% dimethyl sulfoxide was added to be 100%.

Figure 10:
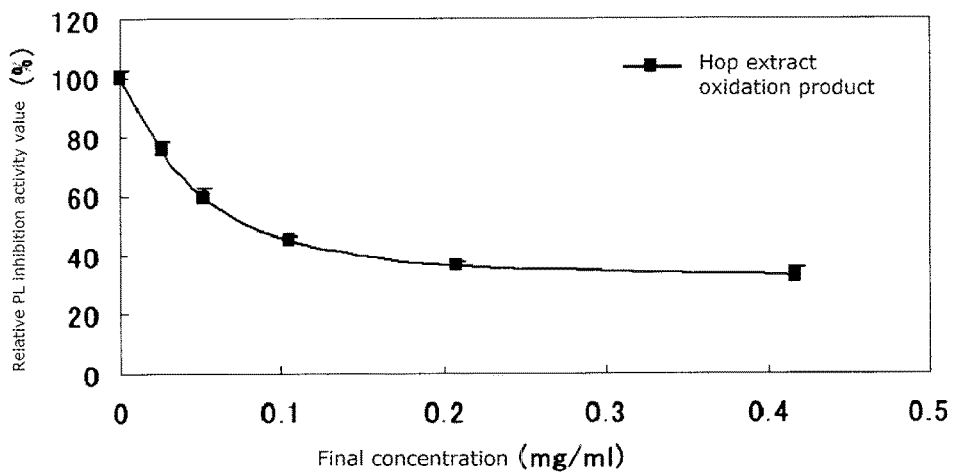
FIG. 10 shows a pancreatic lipase inhibitory activity of a hop extract oxidation-reaction product.

The results showed that the hop extract oxidation-reaction product obtained in Example 1 inhibited the pancreatic lipase activity, and when added in a final concentration of 80.5 μg/ml, the lipase activity decreased down to about 50% (FIG. 10: the pancreatic lipase inhibitory activity of the hop extract oxidation-reaction product; mean±standard deviation). The above results indicated that the hop extract oxidation-reaction product shows a pancreatic lipase activity inhibitory effect.

Next, the hop extract oxidation-reaction products obtained in Examples 2, 3, 5, 7 to 12 were similarly evaluated for a pancreatic lipase activity inhibitory effect. A pancreatic lipase activity inhibitory effect of iso α acid was also evaluated for comparison. An isomerized hop extract (IsoExtract 30%; Hopsteiner) was used for the measurements with iso α acid. The results showed that the hop extract oxidation-reaction products obtained in Examples 2, 3, 5, 7 to 12 all inhibited the pancreatic lipase activity, and when added in a final concentration of 29.2 to 105.8 μg/ml, the lipase activity decreased down to about 50%. In contrast, when iso α acid were added in a final concentration of with 296 μg/ml, the lipase activity decreased down to about 50% (FIG. 11: 50% pancreatic lipase activity inhibitory concentrations of the hop extract oxidation-reaction products (IC50)). The above results showed that the hop extract oxidation-reaction products all had a pancreatic lipase activity inhibitory effect regardless of the types of a raw hop extract and a base material for powdering, and had a stronger activity titer than iso α acid.

Example 16

Water Soluble Formation of Alkaline Metal Salts of the Hop Extract Oxidation-Reaction Product The hop extract oxidation-reaction product obtained in Example 7 (base material FD-101, heated at 80° C. for 24 hours) in an amount of 5 g was added to 25 mL of 0.2 M aqueous sodium hydroxide heated at 50° C. and stirred.

Figure 12:
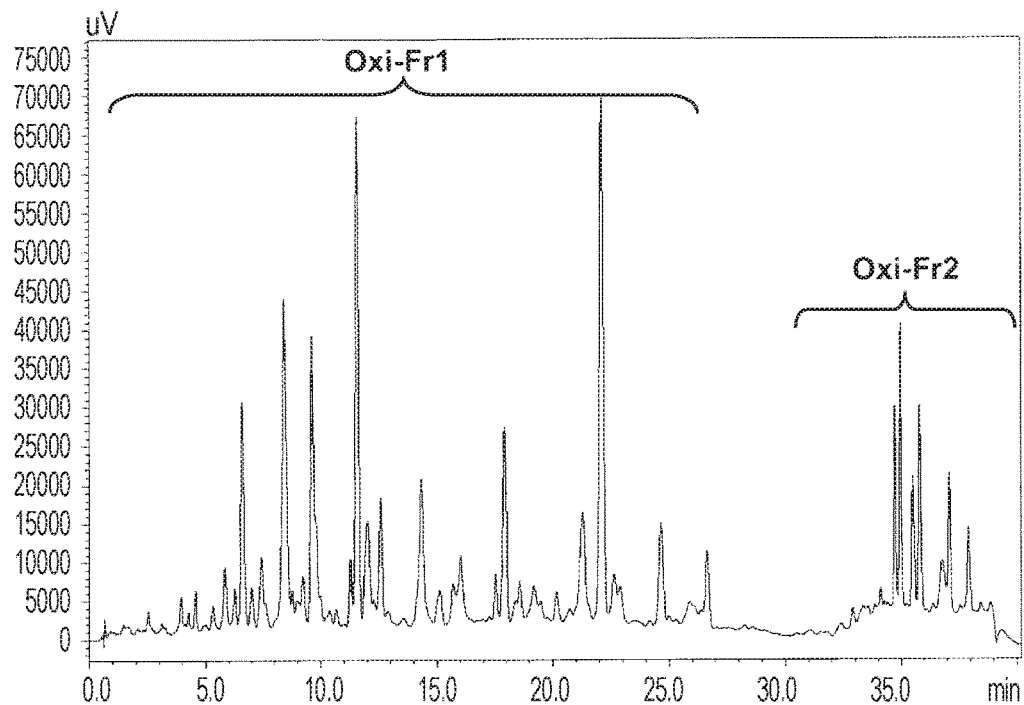
FIG. 12 shows a HPLC chromatogram (detection wavelength: 270 nm) of a water-soluble sodium salt formulation of a hop extract oxidation-reaction product.

The resulting solution was filtered to remove the base material of cellulose to obtain a dark brown and clear aqueous solution of sodium salts of the hop extract oxidation-reaction product (a solid content of oxidated ingredients originated from the hop extract was 5% w/v). The resulting aqueous solution was diluted and analyzed according to the method described in Example 4. The results are shown in FIG. 12. The results showed that the formulation was obtained in which the hop extract oxidation-reaction product was dissolved in water.

Example 17

Structural Analysis of β1-4 Components in the Hop Extract Oxidation-Reaction Product 17-1: Analysis of β1 and β2

HPLC analysis of the hop extract oxidation-reaction product was performed as described in Example 4 to fractionate and purify β1 and β2, which were then analyzed with a mass spectrometer capable of accurate mass determination, and with $^1$H-NMR and $^{13}$C-NMR measurements.

Figure 13:
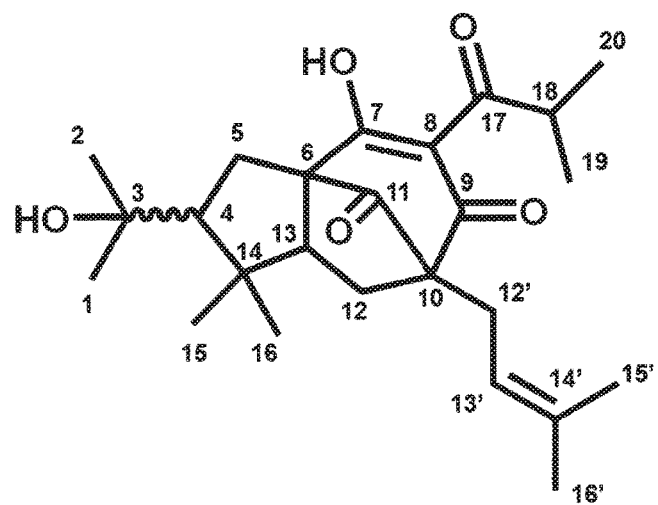
FIG. 13 shows that β1 (Hydroxytricyclocolupone epimer B) and β2 (Hydroxytricyclocolupone epimer A) are stereoisomers in which Position C4 has a different configuration.

The results identified that β1 is any of the compounds of hydroxytricyclocolupone epimer B represented by the formula (I) or a mixture thereof, and that β2 is any of the compounds of hydroxytricyclocolupone epimer A represented by the formula (II) or a mixture thereof. Note that β1 and β2 are stereoisomers in which Position C4 shows different configuration as shown in FIG. 13.

[Formula 7]

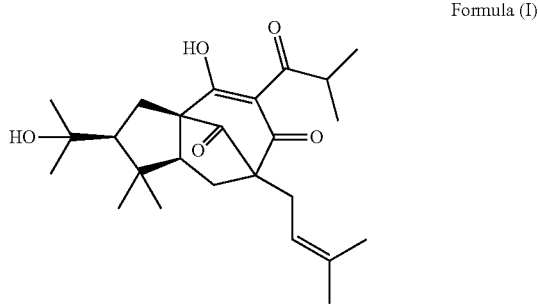

Formula (I)

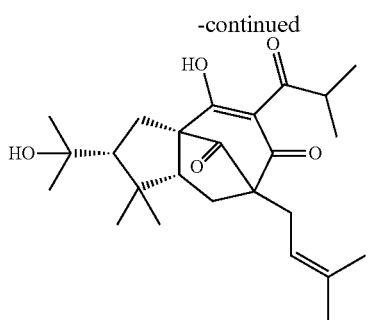

β2

[Formula 8]

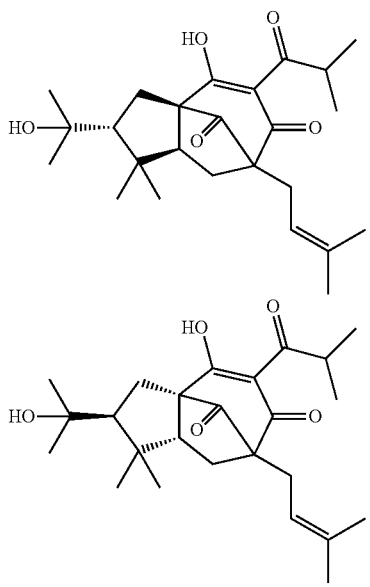

Formula (II)

The results from mass spectrometry, $^1$H-NMR measurements and $^{13}$C-NMR measurements of β1 were as follows.

β1

Mass spectrometry: HR-ESIMS m/z 415.2494 [M-H]$^-$ (calcd for [$C_{25}H_{36}O_5$—H]$^-$, 415.2490)

$^1$H-NMR and $^{13}$C-NMR

TABLE 13

| position | $^1$H (400 MHz, CD3Cl) | $^{13}$C(100 MHz, CD3Cl) |
|---|---|---|
| 1 | 1.34(3H, s) | 30.6 |
| 2 | 1.34(3H, s) | 30.6 |
| 3-OH | — | 73.1 |
| 4 | 1.56(1H, dd) | 58.4 |
| 5 | 2.28(1H, m), 2.43(1H, m) | 23.6 |
| 6 | — | 72.1 |
| 7 | — | 191.7 |
| 8 | — | 109.4 |
| 9-CO | — | 202.1 |
| 10 | — | 65.1 |
| 11-CO | — | 206.1 |
| 12 | 1.92(1H, m), 2.03(1H, m) | 30.8 |
| 13 | 2.36(1H, m) | 56.3 |
| 14 | — | 43.9 |
| 15 | 1.02(3H, s) | 26.6 |
| 16 | 1.11(3H, s) | 26.6 |
| 17-CO | — | 208.7 |

TABLE 13-continued

| position | $^1$H (400 MHz, CD3Cl) | $^{13}$C(100 MHz, CD3Cl) |
|---|---|---|
| 18 | 4.01(1H, m) | 34.8 |
| 19 | 1.14(3H, m) | 18.9 |
| 20 | 1.14(3H, m) | 18.9 |
| 12' | 2.50-2.70(2H, broad) | 26.6 |
| 13' | 5.19(1H, m) | 118.7 |
| 14' | — | 135.1 |
| 15' | 1.68(3H, s) | 18.0 |
| 16' | 1.71(3H, s) | 25.6 |

The results from mass spectrometry, $^1$H-NMR measurements and $^{13}$C-NMR measurements of β2 were as follows.

β2

Mass spectrometry: HR-ESIMS m/z 415.2496 [M-H]$^-$ (calcd for [$C_{25}H_{36}O_5$—H]$^-$, 415.2490)

$^1$H-NMR and $^{13}$C-NMR

TABLE 14

| position | $^1$H (400 MHz, CD3Cl) | $^{13}$C(100 MHz, CD3Cl) |
|---|---|---|
| 1 | 1.33(3H, s) | 31.3 |
| 2 | 1.35(3H, s) | 30.2 |
| 3-OH | — | 72.8 |
| 4 | 1.85(1H, m) | 60.9 |
| 5 | 2.11(1H, m), 2.62(1H, m) | 22.8 |
| 6 | — | 71.7 |
| 7 | — | 191.3 |
| 8 | — | 108.0 |
| 9-CO | — | 200.2 |
| 10 | — | 65.5 |
| 11-CO | — | 206.7 |
| 12 | 1.98(1H, m), 2.59(1H, m) | 28.0 |
| 13 | 2.21(1H, m) | 56.2 |
| 14 | — | 45.2 |
| 15 | 0.78(3H, s) | 17.1 |
| 16 | 1.07(3H, s) | 29.0 |
| 17-CO | — | 209.4 |
| 18 | 4.03(1H, m) | 34.9 |
| 19 | 1.16(3H, d, J = 6.7 Hz) | 18.6 |
| 20 | 1.16(3H, d, J = 6.7 Hz) | 18.8 |
| 12' | 2.48(1H, m), 2.69(1H, m) | 25.0 |
| 13' | 5.20(1H, m) | 118.9 |
| 14' | — | 135.3 |
| 15' | 1.68(3H, s) | 17.9 |
| 16' | 1.71(3H, s) | 25.8 |

17-2: Analysis of β3 and β4

HPLC analysis of the hop extract oxidation-reaction product was performed as described in Example 4 to fractionate and purify β3 and β4, which were then analyzed with a mass spectrometer capable of accurate mass determination, and with $^1$H-NMR and $^{13}$C-NMR measurements.

The eluting position in HPLC was compared with that of β1 according to the method described in J. Agric. Food Chem. 2009, 57, 7480-7489. The results suggested that β3 is n and ad homologs of β1. Further, the mass spectroscopy analysis was conducted and the results identified that β3 was any one of hydroxytricyclolupone epimer B represented by the formula (III) and hydroxytricycloadlupone epimer B represented by the formula (IV) or a mixture thereof.

The results from mass spectroscopy and the chemical formulae of the formula (III) and the formula (IV) are as follows.

β3

Mass spectrometry: HR-ESIMS m/z 429.2650 [M-H]$^-$ (calcd for [$C_{26}H_{38}O_5$—H]$^-$, 429.2647)

Chemical Formula:
Hydroxytricyclolupone Epimer B

[Formula 9]

[Formula (III)]

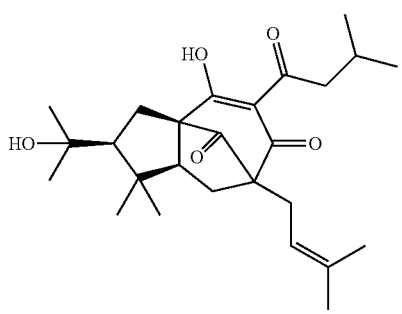

Hydroxytricyclolupone Epimer B

[Formula 10]

Formula (IV)

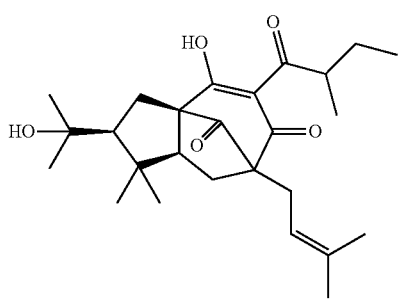

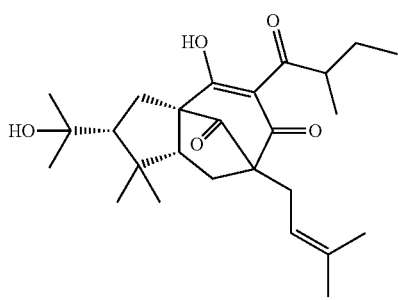

Similarly, the eluting position in HPLC was also compared with that of β2 according to the method described in J. Agric. Food Chem. 2009, 57, 7480-7489. The results suggested that β4 is n and ad homologs of β2. Further, the mass spectroscopy analysis was conducted and the results identified that β4 was any one of hydroxytricyclolupone epimer A represented by the formula (V) and hydroxytricloadlupone epimer A represented by the formula (VI) or a mixture thereof.

The results from mass spectroscopy and the chemical formulae of the formula (V) and the formula (VI) are as follows.

β4

Mass spectrometry: HR-ESIMS m/z 429.2651 [M-H]⁻ (calcd for $[C_{26}H_{38}O_5-H]^-$, 429.2647)

Chemical Formula:
Hydroxytricyclolupone Epimer A

[Formula 11]

Formula (V)

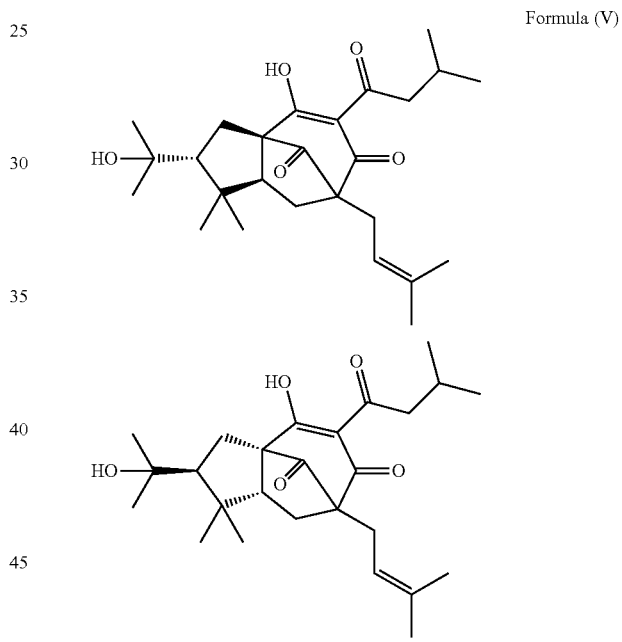

Hydroxytricycloadlupone Epimer A

[Formula 12]

Formula (VI)

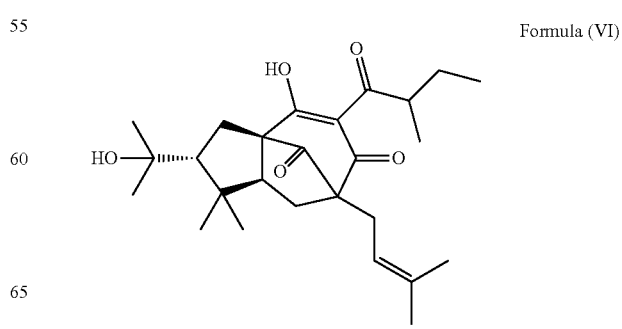

-continued

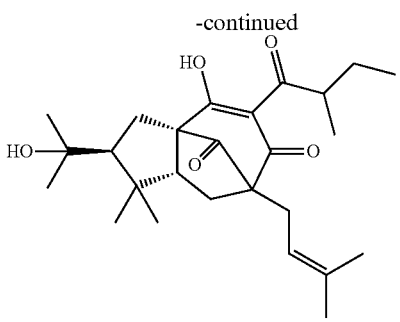

The invention claimed is:

1. A method of suppressing lipid absorption comprising: providing a powdery mixture comprising a hop extract and a base material,
  oxidizing the powdery mixture to obtain the hop extract oxidation-reaction product, and
  administering an effective amount of the hop extract oxidation-reaction product to a mammal including human,
  wherein the hop extract oxidation-reaction product comprises at least one of the components or component groups (A), (B), (C), (D), (E), (F):
  (A) α acid
  (B) iso α acid
  (C) β acid
  (D) Oxi-Fr.1
  (E) Oxi-Fr.2
  (F) β1, β2, β3, β4 wherein each weight ratio of (A) to (F) is (D)/((A)+(B))> 0.1 or more, or (F)/(C)>0.3 or more, or (E)/(C)>2 or more.

2. The method according to claim 1, wherein the hop extract is obtained by extracting a starting material selected from the group consisting of hop, a hop cone, ground product thereof, and combination thereof with supercritical carbon dioxide or an organic solvent.

3. The method according to claim 1, wherein the base material is selected from the group consisting of food and food additives.

4. The method according to claim 3, wherein the base material is at least one selected from the group consisting of saccharides, polysaccharides, inorganic carriers and brewing raw materials.

5. The method according to claim 1, wherein the base material is at least one selected from the group consisting of starch, dextrin, cyclodextrin, cellulose, diatomaceous earth, perlite, activated earth, activated carbon, silica gel, synthetic adsorption resin, a hop and hop lees.

6. The method according to claim 1, wherein a weight ratio of the hop extract and the base material is 1:1 to 1:10.

7. The method according to claim 1, the method further comprising: isolating the hop extract oxidation-reaction product from the oxidized powdery mixture.

8. The method according to claim 1, wherein the hop extract comprises at least one component selected from α acid and iso α acid.

9. The method according to claim 1, wherein the hop extract further comprises β acid.

* * * * *